(12) United States Patent
Loktionov et al.

(10) Patent No.: US 9,448,145 B2
(45) Date of Patent: Sep. 20, 2016

(54) DEVICE AND METHOD FOR NON-INVASIVE COLLECTION OF COLORECTAL MUCOCELLULAR LAYER AND DISEASE DETECTION

(75) Inventors: Alexandre Loktionov, Cambridge (GB); Tatiana Bandaletova, Cambridge (GB); Neil Anderson, Bishops Stortford (GB)

(73) Assignee: Dianodus Limited (GB)

( * ) Notice: Subject to any disclaimer, the term of this patent is extended or adjusted under 35 U.S.C. 154(b) by 92 days.

(21) Appl. No.: 14/115,529

(22) PCT Filed: May 3, 2012

(86) PCT No.: PCT/GB2012/050964
§ 371 (c)(1),
(2), (4) Date: Jan. 21, 2014

(87) PCT Pub. No.: WO2012/150453
PCT Pub. Date: Nov. 8, 2012

(65) Prior Publication Data
US 2014/0154690 A1  Jun. 5, 2014

(30) Foreign Application Priority Data
May 5, 2011 (GB) .................................. 1107466.3

(51) Int. Cl.
*G01N 1/30* (2006.01)
*G01N 33/50* (2006.01)
*G01N 33/68* (2006.01)

(52) U.S. Cl.
CPC ............ *G01N 1/30* (2013.01); *G01N 33/5044* (2013.01); *G01N 33/6893* (2013.01); *G01N 2800/065* (2013.01)

(58) Field of Classification Search
None
See application file for complete search history.

(56) References Cited

U.S. PATENT DOCUMENTS

| | | |
|---|---|---|
| 3,252,762 A | 5/1966 | Adams et al. |
| 3,674,007 A | 7/1972 | Freis |
| 3,735,751 A | 5/1973 | Katz |
| 3,996,006 A | 12/1976 | Pagano |
| 4,092,120 A | 5/1978 | Suovaniemi et al. |
| 4,175,923 A | 11/1979 | Friend |
| 4,199,550 A | 4/1980 | Wielinger et al. |
| 4,259,964 A * | 4/1981 | Levine .......................... 600/371 |
| 4,273,741 A | 6/1981 | Levine |
| 4,333,734 A | 6/1982 | Fleisher |
| 4,367,750 A | 1/1983 | Levine |
| 4,420,353 A | 12/1983 | Levine |
| 4,427,769 A | 1/1984 | Adlercreutz et al. |
| 4,473,079 A | 9/1984 | Jasper et al. |
| 4,521,520 A | 6/1985 | Jacke |
| 4,529,702 A | 7/1985 | Bryan |
| 4,559,949 A | 12/1985 | Levine |
| 4,562,043 A | 12/1985 | Mennen et al. |
| 4,578,358 A | 3/1986 | Oksman et al. |
| 4,578,359 A | 3/1986 | Oksman et al. |
| 4,645,743 A | 2/1987 | Baker et al. |
| 4,808,379 A | 2/1989 | Wardlaw et al. |
| 4,857,457 A | 8/1989 | Shamsuddin et al. |
| 4,879,283 A | 11/1989 | Belzer et al. |
| 4,939,097 A | 7/1990 | Lawrence |
| 5,094,956 A | 3/1992 | Grow et al. |
| 5,096,062 A | 3/1992 | Burkardt et al. |
| 5,198,365 A | 3/1993 | Grow et al. |
| 5,256,571 A | 10/1993 | Hurley et al. |
| 5,380,647 A | 1/1995 | Bahar |
| 5,391,498 A | 2/1995 | Baker et al. |
| 5,416,025 A | 5/1995 | Krepinsky et al. |
| 5,432,053 A | 7/1995 | Berdyaev et al. |
| 5,455,160 A | 10/1995 | Fagerhol et al. |
| 5,552,292 A | 9/1996 | Uchida et al. |
| 5,563,071 A | 10/1996 | Augurt |
| 5,695,945 A | 12/1997 | Tsuji |
| 5,741,650 A | 4/1998 | Lapidus et al. |
| 5,840,584 A | 11/1998 | Waldenburg |
| 5,891,651 A | 4/1999 | Roche et al. |
| 5,910,407 A | 6/1999 | Vogelstein et al. |
| 6,143,529 A | 11/2000 | Lapidus et al. |
| 6,177,251 B1 | 1/2001 | Vogelstein et al. |
| 6,187,546 B1 | 2/2001 | O'Neill et al. |
| 6,187,591 B1 | 2/2001 | Krepinsky et al. |
| 6,203,993 B1 | 3/2001 | Shuber et al. |
| 6,204,375 B1 | 3/2001 | Lader |
| 6,258,541 B1 | 7/2001 | Chapkin et al. |

(Continued)

FOREIGN PATENT DOCUMENTS

EP    002237        1/1981
EP    0022377 A1 *  4/1985

(Continued)

OTHER PUBLICATIONS

Abu-Diab et al. (Comparison between Pernasal Flocked Swabs and Nasopharyngeal Aspirates for Detection of Common Respiratory Viruses in Samples from Children, J Clin Microbiol. Jul. 2008; 46(7): 2414-2417).*

(Continued)

*Primary Examiner* — Aaron Priest
(74) *Attorney, Agent, or Firm* — Tarolli, Sundheim, Covell & Tummino LLP

(57) ABSTRACT

The present invention relates to a device and a method for collecting a sample of colorectal mucocellular layer excreted immediately following the natural act of defaecation from the surface of the anal area of a human subject, and preservation and analysis of the collected sample for detecting diagnostically informative disease biomarkers.

26 Claims, 6 Drawing Sheets

(56) References Cited

U.S. PATENT DOCUMENTS

| | | |
|---|---|---|
| 6,268,136 B1 | 7/2001 | Shuber et al. |
| 6,280,947 B1 | 8/2001 | Shuber et al. |
| 6,300,077 B1 | 10/2001 | Schuber et al. |
| 6,335,193 B1 | 1/2002 | Nair |
| 6,406,857 B1 | 6/2002 | Shuber et al. |
| 6,440,661 B1 | 8/2002 | Øgreid et al. |
| 6,440,706 B1 | 8/2002 | Vogelstein et al. |
| 6,448,002 B1 | 9/2002 | Hillebrand et al. |
| 6,475,738 B2 | 11/2002 | Shuber et al. |
| 6,482,595 B2 | 11/2002 | Shuber et al. |
| 6,498,012 B2 | 12/2002 | Laken |
| 6,503,718 B2 | 1/2003 | Shuber et al. |
| 6,531,319 B1 | 3/2003 | Pant et al. |
| 6,534,280 B1 | 3/2003 | Nair |
| 6,586,177 B1 | 7/2003 | Shuber |
| 6,630,314 B2 | 10/2003 | Nair |
| 6,645,729 B2 | 11/2003 | Nair |
| 6,645,730 B2 | 11/2003 | Nair |
| 6,703,206 B2 | 3/2004 | Pant et al. |
| 6,881,574 B2 | 4/2005 | Nair |
| 6,919,174 B1 | 7/2005 | Shuber |
| 6,964,846 B1 | 11/2005 | Shuber |
| 7,220,538 B2 | 5/2007 | Fischer et al. |
| 7,226,751 B2 | 6/2007 | Erich et al. |
| 7,252,955 B2 | 8/2007 | Pant et al. |
| 7,288,413 B2 | 10/2007 | Goulden |
| 7,432,050 B2 | 10/2008 | Markowitz |
| 7,485,420 B2 | 2/2009 | Markowitz |
| 7,601,348 B2 | 10/2009 | Kannagi et al. |
| 7,749,702 B2 | 7/2010 | Lofton-Day et al. |
| 7,785,772 B2 | 8/2010 | Ahlquist et al. |
| 7,811,757 B2 | 10/2010 | Shuber |
| 7,816,077 B2 | 10/2010 | Kanaoka |
| 7,833,757 B2 | 11/2010 | Steinbert et al. |
| 7,915,015 B2 | 3/2011 | Vogelstein et al. |
| 8,114,027 B2 | 2/2012 | Triva |
| 2001/0024801 A1 | 9/2001 | Nair |
| 2002/0172934 A1* | 11/2002 | Baust et al. ............ 435/2 |
| 2003/0114651 A1* | 6/2003 | Lader ............ 536/23.1 |
| 2004/0267181 A1 | 12/2004 | Tuite et al. |
| 2005/0136553 A1* | 6/2005 | Kaylor et al. ............ 436/518 |
| 2005/0155440 A1 | 7/2005 | Kanjilal et al. |
| 2006/0088862 A1* | 4/2006 | Lee ............ C12Q 1/6886 435/6.14 |
| 2006/0188939 A1 | 8/2006 | Gao |
| 2006/0216830 A1 | 9/2006 | Kikuiri |
| 2008/0034899 A1 | 2/2008 | Kikuiri |
| 2008/0097238 A1* | 4/2008 | Loktionov et al. ............ 600/562 |
| 2008/0199851 A1 | 8/2008 | Egan et al. |
| 2009/0171245 A1 | 7/2009 | Uhl et al. |
| 2009/0197283 A1 | 8/2009 | Gold et al. |
| 2010/0000341 A1 | 1/2010 | Hasegawa et al. |
| 2010/0121046 A1 | 5/2010 | Ahlquist et al. |
| 2011/0087133 A1 | 4/2011 | Ching et al. |
| 2011/0189673 A1 | 8/2011 | Tanigami et al. |

FOREIGN PATENT DOCUMENTS

| | | |
|---|---|---|
| EP | 0643131 | 3/1995 |
| EP | 0643131 A2 * | 11/2001 |
| EP | 1366715 | 12/2003 |
| EP | 1776048 | 4/2007 |
| EP | 1208314 | 10/2009 |
| JP | 2004251851 | 9/2004 |
| JP | 2009115658 | 5/2009 |
| WO | 0006780 | 2/2000 |
| WO | 0191903 | 12/2001 |
| WO | 02059360 | 8/2002 |
| WO | 2004086979 | 10/2004 |
| WO | WO 2004086979 A1 * | 10/2004 |
| WO | 2006039405 | 4/2006 |
| WO | WO 2006039405 A2 * | 4/2006 |
| WO | 2008150962 | 12/2008 |
| WO | 2008152980 | 12/2008 |
| WO | 2010061023 | 6/2010 |
| WO | 2010089538 | 8/2010 |
| WO | WO2011064423 | 6/2011 |

OTHER PUBLICATIONS

Loktionov (Cell exfoliation in the human colon: Myth, reality and implications for colorectal cancer screening, Int J Cancer. Jun. 1, 2007;120(11):2281-9).*

Yang (An Agarose-Gel Based Method for Transporting Cell Lines, Curr Chem Genomics. 2009; 3: 50-53, Dec. 16, 2009).* clinicaltrials.gov (Comparing Two Types of Swabs in Collecting Cell Samples for Anal Pap Tests and Human Papillomavirus Tests in Men Who Have Sex With Men, Sep. 11, 2009, available at http://clinicaltrials.gov/ct2/show/NCT00955591).*

Scansen (Comparison of Polyurethane Foam to Nylon Flocked Swabs for Collection of Secretions from the Anterior Nares in Performance of a Rapid Influenza Virus Antigen Test in a Pediatric Emergency Department, J Clin Microbiol. Mar. 2010; 48(3): 852-856, Jan. 6, 2006).*

Allison et al., "A Comparison of Fecal Occult-Blood Testes for Colorectal-Cancer Screening" 1996, N. Engl. J. Med. vol. 334, pp. 155-159.

Allison et al., "Screening for Colorectal Neoplasms with New Fecal Occult Blood Tests: Update on Performance Characteristics" 2007, J. Natl Cancer Inst., vol. 99, pp. 1462-1470.

Anderson et al. "Protein Biomarkers in Exfoliated Cells Collected from the Human Rectal Mucosa: Implications for Colorectal Disease Detection and Monitoring" 2011 Int J. Colorectal Dis. vol. 26, pp. 1287-1297.

Bader et al., "The Application of Cytology in the Diagnosis of Cancer and the Rectum, Sigmoid, and Descending Colon" 1952, Cancer vol. 5, pp. 307-314.

Bandaletova et al., Isolation of Exfoliated Colonocytes from Human Stool as a New Technique for Colonic Cytology 2002, APMIS vol. 110, pp. 239-246.

Burch et al., "Diagnostic Accuracy of Faecal Occult Blood Tests Used in Screening for Colorectal Cancer: A systematic Review" 2007, J. Med Screen, vol. 14, pp. 132-137.

Collins et al., "Accuracy of Screening for Fecal Occult Blood on a Single Stool Sample Obtained by Digital Rectal Examination: A Comparison with Recommended Sampling Practice" 2005, Ann Intern Med. vol. 142, pp. 81-85.

Duffy et al., "Use of Faecal Markers in Screening for Colorectal Neoplasia: a European Group on Tumor Markers Position Paper" 2011, Int J Cancer, vol. 128, pp. 3-11.

Farlay et al., "Estimates of Worldwide Burden of Cancer in 2008: GLOBOCAN 2008" 2010, Int J. Cancer, vol. 127, pp. 2893-2917.

Foell et al., "Monitoring Disease Activity by Stool Analyses: From Occult Blood to Molecular Markers of Intestinal Inflammation and Damage" 2009, Gut, vol. 58, pp. 859-868.

Glockner et al. "Methylation of TFPI2 in Stool DNA: A Poetential Novel Biomarker for the Detection of Colorectal Cancer" 2009, Cancer Res. vol. 69, pp. 4691-4699.

Greegor "Detection of Silent Colon Cancer in Routine Examination" 1969, CA Cancer J Clin vol. 19, pp. 330-337.

Haeverle et al., "Microfluidic Platforms for Lab-on-a-Chip Applications" 2007, Lab Chip, vol. 7, pp. 1094-1110.

Hamaya et al. "Factors that Contribute to Faecal Cyclooxygenase-2 mRNA Expression in Subjects with Colorectal Cancer" 2010, Br J Cancer, vol. 102, pp. 916-921.

Hellebrekers et al., "GATA4 and GATA5 are Potential Tumor Suppressors and Biomarkers in Colorectal Cancer" 2009, Clin Cancer Res vol. 15, pp. 3990-3997.

Hoff et al., "Contrasting US and European Approaches to Colorectal Cancer Screening: Which is Best" 2010, Gut, vol. 59, pp. 407-414.

Imperiale et al., "Fecal DNA Versus Fecal Occult Blood for Colorectal-Cancer Screening in an Average-Risk Population" 2004, N Engl J Med, vol. 351, pp. 2704-2714.

Itzkowitz, et al., "Incremental Advances in Excremental Cancer Detection Tests" 2009, Gastroenterology, vol. 101, pp. 1225-1227.

Iyengar et al., "Human Stools as a Source of Viable Colonic Epithelial Cells" 1992, FASEB J, vol. 5, pp. 2856-2859.

(56) References Cited

OTHER PUBLICATIONS

Jones et al., "The Epigenomics of Cancer" 2007, Cell, vol. 128, pp. 683-692.
Liberman "Colon Cancer Screening and Surveillance Controversies" 2009, Curr Opin Gastroenterol, vol. 25, pp. 422-427.
Link et al., "Fecal MicroRNAs as Novel Biomarkers for Colon Cancer Screening" 2010 Cancer Epid Biomarkers Prev, vol. 19, pp. 1766-1774.
Loktionov, "Cell Exfoliation in the Human Colon: Myth, Reality and Implicatins for Colorectal Cancer Screening" 2007, Int J. Cancer, vol. 120, pp. 2281-2289.
Loktionov et al., "Quantitation of DNA from Exfoliated Colonocytes Isolated from Human Stool Surface as a Novel Noninvasive Screening Test for Colorectal Cancer" 1988, Clin Cancer Res, vol. 4, pp. 337-342.
Loktionov et al., "Colorectal Cancer Detection by Measuring DNA from Exfoliated Colonocytes Obtained by Direct Contact with Rectal Mucosa" 2009 J Oncol, vol. 34, pp. 301-311.
Loktionov et al., "A Case-Control Study of Colorectal Cancer Detection by Quantification of DNA Isolated from Directly Collected Exfoliated Colonocytes" 2010, Int J Cancer, vol. 126, pp. 1910-1919.
Mao et al., "Disposable Nucleic Acid Biosensors Based on Gold Nanoparticle Probes and Lateral Flow Stip" 2009, Anal Chem, vol. 15, pp. 1660-1668.
Matsuo et al., "Histochemistry of the Surface Mucous Gel Layer of the Human Colon" 1997, Gut, vol. 40, pp. 782-789.
Molodecky et al., "Increasing Incidence and Prevalence of the Inflammatory Bowel Diseases with Time, Based on Systematic Review" 2012, Gastroenterology, vol. 142, pp. 46-54.
Nagasaka et al., "Analysis of Fecal DNA Methylation to Detect Gastrointestinal Neoplasia" 2009, J Natl Cancer Inst, vol. 101, pp. 1244-1258.
Nechvatal et al., "Fecal Collection, Ambient Preservation, and DNA Extraction for PCR Amplification of Bacterial and Human Markers from Human Feces" 2008, J Microbiol Methods, vol. 72, pp. 124-132.
Ransohoff, "How Much Does Colonscopy Reduce Colon Cancer Mortality?" 2009, Ann Intern Med, vol. 150, pp. 50-52.
Richards, "The Size of the Prize for Earlier Diagnosis of Cancer in England" 2009, Br J Cancer, vol. 101, pp. S125-S129.
Wallin et al., "Can DNA Sampling from the Rectal Mucosa be a novel Tool for the Detection of Colorectal Cancer" 2010, Int J Colorectal Dis., vol. 25, pp. 1071-1078.
Whitney et al., "Enhanced Retrieval of DNA from Hunam Fecal Samples Resultes in Improved Performance of Colorectal Cancer Screening Test" 2004, J Mol Diagn, vol. 6, pp. 386-395.
Wong, et al., "Colorectal Cancer: a Model for Epigenetic Tumorigenesis" 2007, Gut, vol. 56, pp. 140-148.
Yu et al., "Exfoliated Cells in Stool: a Source for Reverse Transcription-PCR-Based Analysis of Biomarkers of Gastrointestinal Cancer" 2008, Cancer Epid Biomarkers Prev, vol. 17, pp. 455-458.
Zou, et al., "A Novel Method to Capture Methylated Human DNA from Stool: Implications for Colorectal Cancer Screening" 2007, Clin Chem, vol. 53, pp. 1646-1651.
Abu-Diab et al., "Comparison Between Pernasal Flocked Swabs and Nasopharyngeal Aspirates for Detection of Common Respiratory Viruses in Samples from Children" 2008, Journal of Clinical Microbiology, vol. 46, pp. 2414-2417.
Loktionov "Exfoliation of Cells" Encyclopedia of Cancer, 2008, 7 pages.
Loktionov "Exfoliation of Cells" Encyclopedia of Cancer, 2015, 7 pages.
Bandaletova et al., "Colorectal Mucus Non-Invasively Collected from Patients with Inflammatory Bowel Disease and its Suitability for Diagnostic Cytology" APMIS, 2015, 9 pages.
Loktionov et al., "Colorectal Cancer Detection by Measuring DNA from Exfoliated Colonocytes Obtained by Direct Contact with Rectal Mucosa" International Journal of Oncology, vol. 34, 2009, pp. 301-311.

* cited by examiner

DEVICE AND METHOD FOR NON-INVASIVE COLLECTION OF COLORECTAL MUCOCELLULAR LAYER AND DISEASE DETECTION

FIELD OF THE INVENTION

The present invention relates to a device and a method for collecting a sample of colorectal mucocellular layer excreted during the natural act of defaecation from the surface of the anal area of a human subject, and preservation and analysis of the collected sample for detecting diagnostically informative disease biomarkers.

BACKGROUND OF THE INVENTION

Colon and rectal diseases constitute an extensive group of pathological conditions affecting human large bowel. The importance of early detection and treatment of colorectal diseases is generally recognised, but the range of existing non-invasive screening and diagnostic tests remains strictly limited. Colorectal cancer (CRC) and inflammatory bowel disease (IBD) constitute two major groups of large bowel disorders deserving special attention.

Colorectal cancer (CRC) is one of the most prevalent malignancies with over 1,300,000 new cases detected annually worldwide. The disease mostly affects people over the age of 50 in developed Western countries (Ferlay et al., 2010). Although CRC is the second leading cause of oncological mortality, the disease is curable if detected early. Unfortunately it is often diagnosed late (Richards, 2009) because in many cases clinical manifestations do not appear until advanced CRC stages. For this reason introduction of active screening of asymptomatic people of older (over 50) age groups for CRC presence is regarded as the only possible way to radically improve early cancer detection and patient survival rates.

An ideal cancer screening test should be efficient for disease detection (highly sensitive and specific), non-invasive, safe, well-tolerated, simple, inexpensive, easily repeatable and preferably self-applicable.

Flexible colonoscopy is currently regarded as the most sensitive and specific diagnostic procedure for colorectal tumour detection, but it is an invasive investigation requiring bowel preparation and occasionally causing serious complications (Ransohoff, 2009). It is also important that colonoscopy is an expensive procedure, which should be performed only by highly qualified and specially trained medical professionals. Although flexible colonoscopy is correctly defined as the final common pathway of every colorectal screening program (Lieberman, 2009), the idea of introducing it as the only valid approach to CRC screening advocated by some US experts does not constitute a viable option for most countries (Hoff et al., 2010).

The necessity of a simple, non-invasive and inexpensive test, which could be used as the "first line" of CRC screening is a long-standing problem in clinical medicine. For the last few decades this place has been occupied by Faecal Occult Blood Test (FOBT), first proposed for CRC detection by Greegor (Greegor, 1969). The test is based on the assumption that these tumours often bleed; hence blood presence in stool may indicate bleeding from a colorectal tumour.

U.S. Pat. Nos. 3,252,762; 3,996,006; 4,092,120; 4,199,550; 4,333,734; 4,562,043; 4,939,097; 5,391,498; 5,563,071 describe different versions of the conventional guaiac-based test detecting the presence of haemoglobin in faeces, but these tests may give false-positive results due to the presence of residual haemoglobin in food remnants. A more precise modern version of the test, which is human haemoglobin-specific through immunochemical detection of the protein (globin) component of the human haemoglobin is called Immunochemical Faecal Occult Blood Test (iFOBT) or Faecal Immunochemical Test (FIT). This type of test is exemplified by the methods described in U.S. Pat. Nos. 4,427,769; 5,198,365; 7,288,413.

Although FOBT and iFOBT have some attractive characteristics, being non-invasive, simple, cheap and easily repeatable, application of these tests frequently produces false-positive and especially false-negative results (Allison et al, 1996; 2007; Collins et al, 2005; Burch et al, 2007; Duffy et al, 2011) reflecting the fact that the presence or absence of blood in stool is often unrelated to the presence of CRC (Itzkowitz, 2009). Indeed, in many cases colorectal tumours do not bleed, whereas bleeding from non-neoplastic conditions such as haemorrhoids is very common. Another minor drawback of this test is related to the necessity of temporarily preserving excreted stool for collecting samples for analysis.

The idea of using colonic epithelial cells (colonocytes), which are exfoliated from colonic mucosa and the surface of colorectal tumours, has attracted clinical investigators since the early report of Bader and Papanicolau on cytological differences between material obtained using rectal washings from CRC patients and normal individuals (Bader et al, 1952). Consideration of a possible clinical application of this approach is reflected in U.S. Pat. No. 3,735,751. This patent describes an instrument for rectosigmoid lavage and liquid material collection for cytological investigation. Nevertheless, the lavage-based method of material collection was invasive and unreliable and has never been introduced into clinical practice.

Renewed interest in using exfoliated colonocytes was provoked by studies of P. P. Nair and his group, who claimed that it was possible to isolate "thousands of viable exfoliated colonocytes" from dispersed human stool samples by centrifugation in a density gradient (Iyengar et al., 1991). This assertion constituted the basis of a family of patents obtained by P. P. Nair including U.S. Pat. Nos. 6,355,193; 6,534,280; 6,630,314; 6,645,729; 6,645,730; 6,881,574. Nevertheless, no cytological evidence of colonocyte presence in preparations made according to the patents has been provided by the authors. For this reason the correctness of the key claim regarding viable colonocyte isolation from faeces in significant numbers has been strongly disputed (Loktionov et al, 1998; Loktionov, 2007). Eventually the approach has never been used for clinical purposes.

U.S. Pat. No. 5,981,651 suggested application of epithelium-targeting immunomagnetic beads for recovering epithelial cells from small stool samples, but the method appeared to be complex. Moreover, the recovered cells could only be subjected to qualitative molecular analysis, which still remains to be established as a credible approach to solving clinical problems (see below).

Cell exfoliation is an important mechanism of epithelial tissue renewal, which is relatively inactive in the colorectal epithelium in normal physiological conditions and becomes dramatically activated when neoplastic growth occurs (Loktionov, 2007). Cells shed from normal or neoplastic epithelium are first incorporated into a well oxygenated layer of mucus overlaying the mucosal surface (Matsuo et al., 1997). This mucocellular layer, which provides protection to the exfoliated cells, gradually moves distally alongside faecal flow (Loktionov, 2007; Loktionov et al., 2009). It is inevitable that elements of the mucocellular layer are always excreted with stool during defaecation, but their presence should be mostly confined to stool surface. The validity of this assumption was successfully proven both in experimental (Loktionov et al., 1995) and human (Loktionov et al., 1998) studies and constituted the core of U.S. Pat. No. 6,187,546. The method of exfoliated cell isolation described in that patent provided convincing evidence of the presence of well-preserved easily morphologically identifiable colonocytes in the collected material (Bandaletova et al., 2002). The suggested clinical application of the approach was related to the detection of higher total DNA amount in stool samples from CRC patients compared to cancer-free individuals. Loktionov et al. confirmed that the use of stool surface washes provides much better discrimination between these groups (Loktionov et al., 1998), but the method described in U.S. Pat. No. 6,187,546 required collection and treatment of whole stool samples. This requirement made its wide application for clinical purposes impossible.

Other techniques employing stool DNA for detecting molecular biomarkers of CRC are mostly based upon gene mutation detection initiated following work on mutant k-ras detection in stool samples of some CRC patients. This family of methods involves PCR amplification of selected gene regions of human DNA isolated from stool. Various approaches of this type are described in U.S. Pat. Nos. 5,741,650; 5,910,407; 6,149,529; 6,177,251; 6,203,993; 6,280,947; 6,300,077; 6,406,857; 6,440,661; 6,440,706; 6,448,002; 6,475,738; 6,482,595; 6,498,012; 6,503,718; 6,586,177; 6,919,174; 6,964,846; 7,811,757; 7,833,757; 7,915,015. Nevertheless, no single genetic change is known to be universally present in all colorectal cancers, therefore it became evident that only complex and expensive assays targeting a panel of multiple mutation markers in stool could detect CRC with the specificity approaching 95%. Nevertheless, the sensitivity of the mutation-based panel was only slightly above 50% (Imperiale et al., 2004).

Similarly, hypermethylation of regulatory sequences of several genes was suggested as an alternative or additional CRC biomarker (Jones et al., 2007; Wong et al., 2007). DNA hypermethylation detection in stool samples is described in recent U.S. Pat. Nos. 7,432,050; 7,485,420; 7,749,702; 7,785,772 as well as in WO2010/061023 and WO2010/089538. Although preliminary investigation of some methylation-related assays look promising (Glöckner et al, 2009; Hellebrekers et al., 2009; Nagasaka et al, 2009), DNA methylation assessment methods remain relatively complex and expensive.

Assessment of CRC-associated gene expression changes through analysing stool-derived RNA is emerging as another recent approach (Yu et al., 2008; Hamaya et al., 2010; Link et al., 2010). Methods of this type are already described in U.S. Pat. Nos. 6,258,541 and 7,816,077, however their clinical suitability remains questionable.

Despite growing interest in stool-based assays targeting nucleic acid-associated biomarkers of neoplasia, faecal material remains a problematic substance for detecting changes in the human DNA. The abundance of non-human, bacterial or food-derived DNA and the presence of substances interfering with PCR amplification are well-known problems related to stool sample analysis (Nechvatal et al., 2008). The importance of careful optimization of DNA isolation from stool samples needed to achieve reliable template amplification has also been repeatedly stressed (Whitney et al., 2004; Zou et al., 2007).

Likewise, several immunoassay-based techniques targeting biomarker proteins present in stool have been described in U.S. Pat. Nos. 5,380,647; 5,552,292; 5,695,945; 6,531,319; 6,703,206; 7,226,751; 7,252,955, 7,601,348. These approaches are not sufficiently developed to be used clinically for CRC diagnosis or screening.

Inflammatory bowel disease (IBD) is a group of common chronic disorders involving bowel inflammation. Ulcerative colitis and Crohn's disease are the most important conditions of this group. IBD is usually diagnosed in young adults. In most cases it is characterized by long remissions and incidental flare-ups usually requiring treatment. Currently the highest prevalence of IBD is observed in Europe (827 per 100,000 persons) and North America (568 per 100,000 persons) (Molodecky et al., 2012). All these patients should be monitored for a possible relapse. Those developing relapses are treated, and treatment efficiency assessment is an important task in need of serious improvements. In addition, there is a frequent necessity of distinguishing between extremely common functional gastrointestinal disorders, such as irritable bowel syndrome and IBD. Unfortunately, repeated diagnostic colonoscopies may be dangerous in IBD patients, and the range of non-invasive tests available for these purposes is very limited and includes only the use of serologic and faecal biomarkers, detection of which requires blood or stool collection and laboratory analysis (Foell et al., 2009). The most reliable method among those used for faecal sample analysis is the detection of neutrophil-specific protein calprotectin using ELISA assay described in U.S. Pat. No. 5,455,160 by Fagerhol et al.

It was also repeatedly demonstrated that in IBD patients inflammatory cells are present in abundance in the mucocellular layer overlaying colorectal mucosa (Loktionov, 2007: Loktionov et al., 2009; Loktionov et al., 2010; Anderson et al., 2011) and are excreted during defaecation.

The information presented above indicates that exfoliated cells, inflammatory cells and cell fragments found in the colonic mucocellular layer represent the informative element of the bowel contents in terms of detecting CRC and IBD, whereas the presence of stool-derived substances interferes with analytical procedures. For this reason attempts to obtain material less contaminated with faeces were undertaken by applying minimally invasive collection procedures involving a direct contact between a material-collecting surface and the rectal mucosa, which is the inner lining of the rectum.

Traditional digital rectal examination used in practical medicine for millennia is the simplest way of providing a contact between gloved finger of the examiner and patient's rectal mucosa. U.S. Pat. Nos. 4,857,457; 5,416,025; 6,187,591 proposed using this straightforward approach for obtaining rectal mucus, which is then analysed for the presence of a number of substances regarded as disease biomarkers.

In a more recent European Pat. No. EP1776048 a device equipped with an inflatable balloon, which is introduced to the rectum through a proctoscope is described. A rectal mucocellular layer sample is collected by inflating the balloon, which comes into contact with the surface of the rectal mucosa. Collection of well preserved colonic cells by this method was well documented in a few publications (Loktionov, 2007; Loktionov et al., 2009; Loktionov et al., 2010). The use of quantification of DNA isolated from collected material was successfully employed for CRC detection (Loktionov et al., 2009; Loktionov et al., 2010; Wallin et al., 2010), but this method is unlikely to be suitable for CRC screening purposes due to the proctoscopy requirement making the approach invasive.

Given the questionable basis of the FOBT, relying exclusively on blood presence detection (Itzkowitz, 2009), measurement of biomarkers obtained from cells found in the mucocellular layer of the large bowel appears to be the most promising analytical pathway to devising a really efficient non-invasive approach to CRC screening and detection of IBD. Unfortunately efforts of the scientific community in this direction were predominantly concentrated on stool-based methods with little thought devoted to the development of simple techniques for material self-collection by tested individuals and eventual creation of point-of-care tests or self-testing systems for CRC screening and IBD detection and monitoring.

Material self-collection and development of self-testing for CRC was considered in the context of FOBT by several authors. The generally accepted preparation of stool samples for FOBT normally involves temporary preservation of the whole excreted stool and transfer of its small portion on a special chemically treated card using a spatula, spoon or brush (see U.S. Pat. Nos. 3,252,762; 3,996,006; 4,092,120; 4,199,550; 4,333,734; 4,939,097; 4,562,043; 5,391,498; 5,563,071). A family of alternative FOBT modifications based on the use of faecal material obtained by wiping the anal area following defaecation with sheet-like soft multi-layered composites was proposed by several authors. These versions of FOBT are described in the U.S. Pat. Nos. 4,259,964; 4,273,741; 4,367,750; 4,420,353; 4,559,949; 4,578,358; 4,578,359; 4,645,743; 4,808,379; 5,840,584; and European Pat. No. EP2108314. All these modifications providing sample self-collection were designed exclusively with the purpose of obtaining faecal material and detecting occult blood in it. Among them only the device described by Waldenburg in U.S. Pat. No. 5,840,584 could potentially be used for FOBT self-testing. Other early versions of FOBT designed for self-testing were based upon using indicator devices placed in the bowl of a toilet (U.S. Pat. Nos. 4,175,923 and 4,521,520). None of the latter devices has been used for clinical purposes as well as a point-of care version of the FOBT test on an examination glove proposed to be used immediately following rectal examination and described in U.S. Pat. No. 4,473,079.

The presented background information indicates that FOBT in different versions currently presents the only available option for non-invasive CRC screening. FOBT sensitivity and specificity are not sufficient, therefore an alternative test using more reliable CRC biomarkers than blood presence in stool could replace FOBT if shown to be more sensitive and specific than the latter, being at the same time inexpensive, simple and suitable for point-of-care or self-testing applications. Analysing the mucocellular layer containing exfoliated cells, cell fragments and biomolecules reflecting the state of the colorectal mucosa undoubtedly provides the best chance of detecting CRC presence. Likewise, IBD detection and inflammation activity assessment can be greatly facilitated by applying this approach. However, as discussed above, there are at present no methods for reliably sampling the mucocellular layer using non-invasive techniques. Therefore, the most challenging task in testing the mucocellular layer is to devise a non-invasive, simple and inexpensive technique for its sampling and analysis. The present invention addresses this problem.

For convenience, a list of references cited herein follows:

U.S. PATENT DOCUMENTS

| | | |
|---|---|---|
| 3,252,762 | May 1966 | Adams et al. |
| 3,674,007 | July 1972 | Freis |
| 3,735,751 | May 1973 | Katz |
| 3,996,006 | December 1976 | Pagano |
| 4,092,120 | May 1978 | Suovaniemi et al. |
| 4,175,923 | November 1979 | Friend |
| 4,199,550 | April 1980 | Wielinger et al. |
| 4,259,964 | April 1981 | Levine |
| 4,273,741 | June 1981 | Levine |
| 4,333,734 | June 1982 | Fleisher |
| 4,367,750 | January 1983 | Levine |
| 4,420,353 | December 1983 | Levine |
| 4,427,769 | January 1984 | Adlercreutz et al. |
| 4,473,079 | September 1984 | Jasper et al. |
| 4,521,520 | June 1985 | Jacke |
| 4,529,702 | July 1985 | Bryan |
| 4,559,949 | December 1985 | Levine |
| 4,562,043 | December 1985 | Mennen et al. |
| 4,578,358 | March 1986 | Oksman et al. |
| 4,578,359 | March 1986 | Oksman et al. |
| 4,645,743 | February 1987 | Baker et al. |
| 4,808,379 | February 1989 | Wardlaw et al. |
| 4,857,457 | August 1989 | Shamsuddin et al. |
| 4,879,283 | November 1989 | Belzer et al. |
| 4,939,097 | July 1990 | Lawrence |
| 5,096,062 | March 1992 | Burkhardt et al. |
| 5,094,956 | March 1992 | Grow et al. |
| 5,198,365 | March 1993 | Grow et al. |
| 5,256,571 | October 1993 | Hurley et al. |
| 5,380,647 | January 1995 | Bahar |
| 5,391,498 | February 1995 | Baker et al. |
| 5,416,025 | May 1995 | Krepinsky et al. |
| 5,432,053 | July 1995 | Berdyaev et al. |
| 5,455,160 | October 1995 | Fagerhol et al. |
| 5,552,292 | September 1996 | Uchida et al. |
| 5,563,071 | October 1996 | Augurt |
| 5,565,317 | October 1996 | Dohi et al. |
| 5,695,945 | December 1997 | Tsuji |
| 5,741,650 | April 1998 | Lapidus et al. |
| 5,840,584 | November 1998 | Waldenburg |
| 5,891,651 | April 1999 | Roche et al. |
| 5,910,407 | June 1999 | Vogelstein et al. |
| 6,143,529 | November 2000 | Lapidus et al. |
| 6,187,546 | February 2001 | O'Neill et al. |
| 6,187,591 | February 2001 | Krepinsky et al. |
| 6,177,251 | January 2001 | Vogelstein et al. |
| 6,203,993 | March 2001 | Shuber et al. |
| 6,204,375 | March 2001 | Lader |
| 6,258,541 | July 2001 | Chapkin et al. |
| 6,268,136 | July 2001 | Shuber et al. |
| 6,280,947 | August 2001 | Shuber et al. |
| 6,300,077 | October 2001 | Shuber et al. |
| 6,335,193 | January 2002 | Nair |
| 6,406,857 | June 2002 | Shuber et al. |
| 6,440,661 | August 2002 | Øgreid et al. |
| 6,440,706 | August 2002 | Vogelstein et al. |
| 6,448,002 | September 2002 | Hillebrand et al. |
| 6,475,738 | November 2002 | Shuber et al. |
| 6,482,595 | November 2002 | Shuber et al. |
| 6,498,012 | December 2002 | Laken |
| 6,503,718 | January 2003 | Shuber et al. |
| 6,531,319 | March 2003 | Pant et al. |
| 6,534,280 | March 2003 | Nair |
| 6,586,177 | July 2003 | Shuber |
| 6,630,314 | October 2003 | Nair |
| 6,645,729 | November 2003 | Nair |
| 6,645,730 | November 2003 | Nair |
| 6,703,206 | March 2004 | Pant et al. |
| 6,881,574 | April 2005 | Nair |
| 6,919,174 | July 2005 | Shuber |
| 6,964,846 | November 2005 | Shuber |
| 7,220,538 | May 2007 | Fischer et al. |
| 7,226,751 | June 2007 | Erich et al. |
| 7,252,955 | August 2007 | Pant et al. |
| 7,288,413 | October 2007 | Goulden |

-continued

| | | |
|---|---|---|
| 7,432,050 | October 2008 | Markowitz |
| 7,485,420 | February 2009 | Markowitz |
| 7,601,348 | October 2009 | Kannagi et al. |
| 7,749,702 | July 2010 | Lofton-Day et al. |
| 7,785,772 | August 2010 | Ahlquist et al. |
| 7,811,757 | October 2010 | Shuber |
| 7,816,077 | October 2010 | Kanaoka |
| 7,833,757 | November 2010 | Steinberg et al. |
| 7,915,015 | March 2011 | Vogelstein et al. |
| 8,114,027 | February 2012 | Triva |

US PATENT APPLICATIONS

| | | |
|---|---|---|
| US2001/024801 | January 2001 | Nair |
| US2004/267181 | June 2004 | Tuite et al. |
| US2006/216830 | March 2005 | Alfresa Pharma Corp. |
| US2005/155440 | June 2005 | Kanjilal et al. |
| US2008/034899 | June 2005 | Alfresa Pharma Corp. |
| US2008/097238 | July 2005 | Loktionov et al. |
| US2006/088862 | September 2005 | Lee |
| US2006/188939 | February 2006 | Gao |
| US2010/000341 | December 2006 | Nipro Corp. |
| US2008/199851 | February 2007 | Egan et al. |
| US2009/171245 | May 2007 | Uhl et al. |
| US2009/197283 | September 2008 | Gold et al. |
| US2010/121046 | September 2009 | Mayo Foundation |
| US2011/087133 | April 2010 | Ching et al. |
| US2011/189673 | February 2011 | Olympus Corp. |

OTHER PATENT DOCUMENTS

| | | |
|---|---|---|
| JP2004251851 | February 2003 | Japan Clinical Lab Inc. |
| EP1366715 | May 2003 | Sentinel CH S.R.L |
| EP1776048 | April 2007 | Loktionov et al. |
| WO08/152980 | June 2007 | Olympus Corp. |
| JP2009115658 | November 2007 | Olympus Corp. |
| EP2108314 | October 2009 | LaStella |
| WO2010/061023 | June 2010 | Capella |
| WO2010/089538 | August 2010 | Joost |
| WO11/064423 | September 2010 | Durviz et al |

OTHER PUBLICATIONS

Allison et al. (1996) N Engl J Med 334: 155-159.
Allison et al. (2007) J Natl Cancer Inst 99: 1462-1470.
Anderson et al. (2011) Int J Colorectal Dis 26: 1287-1297.
Bader et al. (1952) Cancer 5: 307-314.
Bandaletova et al. (2002) APMIS 110: 239-246.
Burch et al. (2007) J Med Screen 14: 132-137.
Collins et al. (2005) Ann Intern Med 142: 81-85.
Duffy et al. (2011) Int J Cancer 128: 3-11.
Ferlay et al. (2010) Int. J. Cancer 127: 2893-2917.
Foell et al. (2009) Gut 58: 859-868.
Glöckner et al. (2009) Cancer Res 69: 4691-4699.
Greegor (1969) CA Cancer J Clin 19: 330-337.
Haeberle et al (2007) Lab Chip 7: 1094-1110.
Hamaya et al. (2010) Br J Cancer 102: 916-921.
Hellebrekers et al. (2009) Clin Cancer Res 15: 3990-3997.
Hoff et al. (2010) Gut 59: 407-414.
Imperiale et al. (2004) N Engl J Med 351: 2704-2714.
Itzkowitz (2009) Gastroenterology 101: 1225-1227.
Iyengar et al. (1992) FASEB J 5: 2856-2859.
Jones et al. (2007) Cell 128: 683-692.
Lieberman. (2009) Curr Opin Gastroenterol 25: 422-427.
Link et al. (2010) Cancer Epid Biomarkers Prev 19: 1766-1774.
Loktionov (2007) Int J Cancer 120: 2281-2289.
Loktionov et al., (1995) Int J Oncol 6: 437-445.
Loktionov et al. (1998) Clin Cancer Res 4: 337-342.
Loktionov et al. (2009) Int J Oncol 34: 301-311.
Loktionov et al. (2010) Int J Cancer 126: 1910-1919.
Mao et al. (2009) Anal Chem 15: 1660-1668.
Matsuo et al. (1997) Gut 40: 782-789.
Molodecky et al. (2012) Gastroenterology 142: 46-54.
Nagasaka et al. (2009) J Natl Cancer Inst 101: 1244-1258.
Nechvatal et al. (2008) J Microbiol Methods 72: 124-132.
Ransohoff (2009) Ann Intern Med 150: 50-52.
Richards (2009) Br J Cancer 101: S125-S129.
Wallin et al. (2010) Int J Colorectal Dis 25: 1071-1078.
Whitney et al. (2004) J Mol Diagn 6: 386-395.
Wong et al. (2007) Gut 56: 140-148.
Yu et al. (2008) Cancer Epid Biomarkers Prev 17: 455-458.
Zou et al. (2007) Clin Chem 53: 1646-1651.

SUMMARY OF THE INVENTION

According to a first aspect of the present invention, there is provided a non-invasive method for collecting a sample of intestinal or bowel cells or cell fragments comprising taking a swab of mucocellular layer material originating from said bowel or intestine from the surface of the anal area in the vicinity of the exterior opening of the anal canal, wherein said swab is taken following defaecation. More preferably, the intestinal or bowel cells originate from the interior wall of the lower intestines or large bowel. Furthermore, preferably, the mucocellular layer originates from the lower intestines.

In one embodiment, the swab is taken within 5 minutes of defaecation and prior to cleaning the anal area. More preferably, the swab is taken within 4, 3, 2 or 1 minute of defaecation.

The method may further comprise placing said swab of mucocellular layer material in a storage medium or a lysis medium. The storage medium may comprise a concentrated salt solution. The salt solution may be ammonium sulphate. Alternatively, the highly concentrated salt solution may be sodium citrate, ammonium bisulphate, ammonium acetate or sodium chloride. The storage medium may be a liquid (e.g solutions, suspensions or emulsions) or a gel.

A further aspect of the invention provides a method for diagnosing bowel disease comprising collecting a sample of intestinal or bowel cells or cell fragments using the method of any preceding claim and analysing said sample for the presence of one or more bowel disease-specific markers (i.e. biomarkers).

Analysis of bowel disease-specific markers may include an analysis of cell morphology of intact cells (e.g. cell type, shape, size, numbers and/or the in situ presence of disease-specific DNA sequences, RNAs or proteins) and/or detecting and measuring the presence of one or more bowel disease-specific biomarkers released from lysed cells. The bowel disease-specific biomarkers may include overall amount of DNA and a range of specific molecular markers comprising DNA-associated genetic markers related to either mutations or epigenetic changes such as DNA methylation, RNA-associated genetic markers reflecting expression levels of specific genes, and protein markers indicating the presence of specific enzymes or regulatory proteins. DNA-associated genetic markers related to mutations may be detected and measured for such genes as APC, AXIN2, KRAS, TP53

(p53), STK11, PTEN, BRCA1, BRCA2, CHEK2 BMPR1A, PIC3CA, SMAD4 (DPC4), MLH1, TACSTD1, MYH (Mu-tYH), MSH2, MSH6, PMS2, BLM, KIT, PDGFRA, NOD2 (CARD15), ATG16L1, IL-23, IL12B, STAT3, NKX2-3, TGFBR2, IGF2R, BAX, ACVR2, SEC63, AIM2, KIAA0977, PA2G4/EBP1, hBUB1, ATM, ATR, STK15, PLK1, CDC.

DNA-associated genetic markers related to aberrant methylation of specific gene regions may be detected and measured for such genes as SFRP1, SFRP2, GATA4, GATA5, TFPI2, oncostatin M specific receptor β, RASSF2, CDKN2, NDGR4, MAL, O-6-methylguanine-DNA methyltransferase, integrin α4, septin 9, vimentin, CDX1, TIMP3. RNA-associated genetic markers reflecting gene expression may be detected and measured for such genes as HMGIV, c-Myc, CTP-synthetase, surviving, VEGF, B-myb, ATDC, EB1, BRCA2, MAPK3, Carbonic anhydrase II, Carcinoembryonic antigen-related cell adhesion molecule 1, TRAIL, ADAMTS1. Protein markers may include such proteins as M2PK, calprotectin, lactoferrin, S100A12, myeloperoxidase, polymorphonuclear elastase, eosinophil cationic protein, eosinophil-derived neurotoxin (EDN), lysozyme, cytokeratin 18, VEGF, TNFα, IL6, IL1, IL8, D-dimer. Detection and measurement of the presence of one or more bowel disease-specific biomarkers may include detection and measurement of the DNA, RNA or the protein of disease-specific markers, in particular, the detection and measurement of one of the above molecular markers. A range of quantitative approaches including nucleic acid hybridisation-based techniques, various versions of real-time PCR (for nucleic acid analysis), immunochemical techniques (for proteins) and biosensor-based methods can be used for biomarker measurement.

An additional aspect of the invention provides a method for screening for bowel disease using the method described above. The method for screening includes screening asymptomatic individuals.

A further aspect of the present invention provides a method for monitoring bowel disease using the method described above. In particular, the method for monitoring includes monitoring the progression of the bowel disorder.

A further aspect of the invention provides a method for assessing the efficiency of bowel disease treatment using the method described above. In particular, the method for treatment efficiency assessment includes evaluation of the level of activity of bowel inflammation. Quantitative or semi-quantitative techniques providing biomarker measurement need to be used for this purpose.

Bowel disease can include colorectal disorders, including colorectal cancer, anal cancer and inflammatory bowel disease. Inflammatory bowel disease may include Crohn's disease and ulcerative colitis (UC). Inflammatory bowel disease may also include microscopic colitis (comprising collagenous colitis and lymphocytic colitis), ischaemic colitis, diversion colitis, allergic colitis and Behçet's disease. Bowel disease can also include colorectal polyps, celiac disease and functional disorders such as Irritable Bowel Syndrome.

Another aspect of the invention provides a device for use in the method described above wherein the device comprises a swab in combination with a storage or lysis medium.

The swab may also comprise a porous sample collection material coupled to a lateral flow assay.

The sample collection material may be flocked nylon.

The device may further comprise a gel plug. Preferably the gel plug is used in combination with a liquid storage medium or liquid lysis medium.

Another aspect of the invention provides a device for use in the method described above comprising a porous sample collection material coupled to a lateral flow assay. The device may further comprise a sample holder with a cap, wherein said lateral assay system comprises a lateral assay strip between said cap and said sample collection material and wherein said cap includes a system to promote capillary action.

The lateral flow assay may be an immunoassay or a nucleic acid hybridisation assay. Where the lateral flow assay is an immunoassay, the lateral flow assay strip comprises antibodies specific to bowel disease-specific molecular markers. Where the lateral flow assay is intended to quantify nucleic acids, the assay strip may comprise oligonucleotide probes specific for bowel disease genetic markers. Alternatively probes comprising oligonucleotides or nucleotide triphosphates labelled for example with biotin or digoxygenin may be included in the medium and detected using complementary molecules such as gold- or latex-labelled streptavidin or antibodies, in absorbent pad associated with the flow strip or immobilised on the flow strip itself. Alternatively peptide nucleic acids, either sequence-specific or random, could be used as the detection component of the lateral flow strip. The bowel-disease specific markers may be the markers described above.

In a further aspect of the invention, there is provided a kit for collecting a sample of intestinal or bowel cells comprising a device comprising a porous sample collection material coupled to a lateral flow assay system and a buffer to dissolve and lyse the sample.

In the embodiment in which the collected sample is stored for subsequent laboratory analysis the storage medium is a medium suitable for preserving the sample of intestinal or bowel cells. The storage medium may comprise a concentrated salt solution. The salt solution may be ammonium salt solutions. Alternatively, the concentrated salt solution may be sodium citrate, ammonium bisulphate, ammonium acetate or sodium chloride. The storage medium may be a liquid (e.g solutions, suspensions or emulsions) or a gel.

The lysis buffer is any buffer suitable for lysing cells. In particular, the lysis buffer may comprise a buffer solution, a surfactant and/or a detergent and a chelating agent.

The lysis buffer may also comprise oligonucleotide primers specific for the detection of bowel disease-specific genetic markers together with reagents suitable for performing isothermal PCR (polymerase chain reaction). In particular, the oligonucleotide primers may be specific for the detection of the bowel disease specific genes described above.

In another aspect of the invention, where samples need to be stored for return to a laboratory rather than analysed immediately, there is provided a liquid or gel medium for use in the above method, wherein the medium comprises a concentrated salt solution.

The salt solution may be ammonium salt solutions. Alternatively, the concentrated salt solution may be sodium citrate, ammonium bisulphate, ammonium acetate or sodium chloride.

The gel medium may further comprise a gelling agent. The gelling agent may be agarose, acrylamide, gelatine or pectin. Preferably, the gelling agent is agarose. More preferably, the gelling agent is 0.25% agarose.

In a preferred embodiment, the gel comprises no more than 25% ammonium sulphate v/v and no more than 0.25% agarose w/v. Alternatively, the gel comprises 25% ammonium sulphate v/v and 0.25% agarose w/v.

Preferably, the gel medium comprises a salt solution, wherein the salt solution is non-saturated.

Additional Objectives of the Present Invention

It is the objective of this invention to provide a device and a method for collecting a sample of colorectal mucocellular layer from the surface of the anal area of a human subject and testing the said sample for the presence of colorectal disease biomarkers also referred to herein as disease-specific markers.

The invention provides sampling devices, kits, a method of sampling, methods of sample preservation, methods of biomarker determination and methods of disease detection, screening, diagnosis and monitoring as defined in the appended independent claims. Preferred, advantageous and optional features of the invention are described in the dependent claims.

Embodiments of the present invention satisfy the needs explained in the prior art (background) section of this document. For example, according to one embodiment, a device for collecting fragments of large bowel mucocellular layer from the surface of the anal area may be a swab consisting of a rod and a piece of absorbing material (also referred to herein as a sample-collecting element or a porous sample collection material) attached to its distal end.

Such a device can be used for non-invasive self-collection of material rich in fragments of large bowel mucocellular layer excreted during the natural act of defaecation and remaining on the surface of the anal area immediately following the said act. Material collection can be achieved by a short contact between the sample-collecting element of the device and the surface of the anal area before cleaning the said area.

In a further aspect of the invention, the proximal end of the swab rod of the device is attached to the inner surface of a cap compatible with a laboratory tube.

In a further aspect of the invention, the cap attached to the proximal end of the swab rod is a screw-cap.

In a second embodiment of the invention, the rod of the swab is replaced with a lateral flow test strip or a lateral flow assay system forming a lateral flow strip device.

In a further aspect of the invention, the screw cap attached to the end of the lateral flow test strip contains a wicking pad.

In a further aspect of the invention, the lateral flow test device is supplied inside an empty laboratory tube providing protection of the sample-collecting element from external contamination.

In a further aspect of the invention, the lateral flow test device is disposable.

In a third embodiment of the invention, the tube containing the swab or lateral flow strip device constitutes an element of a kit.

In a further aspect of the invention, the kit comprises the swab- or lateral flow strip device-containing tube and a similar tube containing a buffer or a medium.

In a further aspect of the invention, the buffer or medium is a cell-preserving or fixing medium providing cell structure preservation for further cytological and/or immunocytochemical analysis. Such a buffer or medium is referred to herein as a preserving or storage medium.

In a further aspect of the invention, the buffer is a lysis buffer or medium providing cell lysis and biomolecule release for further analysis.

In a further aspect of the invention, the buffer is a stabilising medium providing protein and nucleic acid stabilisation for further protein and/or nucleic acid analysis. Such a buffer or medium may also be considered a storage medium.

In a further aspect of the invention the storage buffer or medium contains a high salt concentration precipitating proteins in the sample, preventing autolysis, putrefaction and inhibiting microbial action.

In a further aspect of the invention the storage or stabilising buffer or medium is a liquid.

In a further aspect of the invention the storage stabilising buffer or medium is a liquid sealed under a plug of gel.

In a further aspect of the invention the storage or stabilising buffer is a gel

In a further aspect of the invention the storage or stabilising buffer impregnates a sponge.

In a further aspect of the invention, the lateral flow strip device of the kit contains an immunoassay for quantitative identification of proteins.

In a further aspect of the invention, the lateral flow strip device of the kit contains components for reactions for qualitative and quantitative identification of DNA.

In a further aspect of the invention, the quantitative identification of DNA is limited to human-specific DNA.

In a further aspect of the invention, the kit contains reagents for performing polymerase chain reaction (PCR) including oligonucleotide primers, enzymes, dNTPs and appropriate buffering solutions.

Any of the devices or kits described above are suitable for collecting biological samples from the natural body orifices including urethra, vagina, nostrils, external ear and oral cavity, and in particular anus.

Any of the devices or kits described above is suitable to use on animals, and in particular humans.

Any of the devices or kits described above is suitable for sampling fragments of large bowel mucocellular layer containing exfoliated cells originating from colon (e.g. colonocytes and free cells comprising inflammatory cells).

In a fourth embodiment of the invention a method of sampling fragments of large bowel mucocellular layer from the surface of the anal area immediately following the natural act of defaecation is provided. The method comprises the steps of:

Following the natural act of defaecation bringing the sample-collecting element of the sampling device into proximity with the anal area;

Contacting the sample-collecting surface with the surface of mucosa/skin covered with the remnants of excreted material rich in fragments of large bowel mucocellular layer;

Removing the sampling device from proximity with the anal area without making contact with any other surface;

In a further aspect of the invention the method comprises the steps of:

Inserting the sampling device in a tube containing a medium or a buffer;

Immersing the material-collecting element in the medium or buffer;

Hermetically sealing the tube;

Any of the methods described above are suitable for sampling body fluids/biological materials from the natural body orifices including urethra, vagina, nostrils, external ear, oral cavity and in particular the anus.

Sampling large bowel mucocellular layer fragments from the anal/perianal area is generally possible only immediately following the natural act of defaecation.

Sampling large bowel mucocellular layer fragments from the anal/perianal area following the natural act of defaecation is best performed by self-sampling.

In a fifth embodiment of the invention, a method of sample analysis is provided. The method comprising any of the methods described above and further comprising recovering the collected sample from the sampling device and performing an analytical assay on the sample.

In a further aspect of the invention, the method of sample analysis is selected from direct DNA quantitation, DNA isolation, quantitation and molecular analysis, RNA isolation and molecular analysis, protein quantification by immunoassays or cytological investigation.

In a further aspect of the invention, the method of sample analysis can be performed using the lateral flow strip device.

In a further aspect of the invention, the method of sample analysis on the lateral flow strip device is an immunoassay for quantitative identification of a specific protein.

In a further aspect of the invention, the method of sample analysis on the lateral flow strip device is a DNA hybridization-based assay for quantitation of specific DNA sequences or quantification of total human DNA concentration.

In a further aspect of the invention, the method of sample analysis on the lateral flow strip device is the selective quantitation of human-specific DNA in the presence of contaminating non-human DNA molecules.

In a further aspect of the invention, the method of sample analysis involves DNA amplification using PCR.

In a further aspect of the invention, the PCR can be loop-mediated isothermal amplification (LAMP).

In a further aspect of the invention, the method of sample analysis can be performed as a "point of care" test.

In a further aspect of the invention, the method of sample analysis can be performed as a self-testing assay.

In a sixth embodiment of the invention, a method of disease detection in symptomatic patients is provided. The method comprising any of the methods described above and further comprising a conclusion on the presence or absence of a disease.

In a further aspect of the invention, the method of disease detection is provided for detecting colorectal disease.

In a further aspect of the invention, the method of disease detection is provided for detecting colorectal cancer (CRC).

In a further aspect of the invention, the method of disease detection is provided for detecting anal cancer.

In a further aspect of the invention, the method of disease detection is provided for detecting Inflammatory Bowel Disease (IBD).

In a further aspect of the invention, the method of disease detection is provided for detecting advanced colorectal polyps.

In a seventh embodiment of the invention, a method of disease monitoring is provided. The method comprising any of the methods described above and further comprising conclusion on the progress of a disease.

In a further aspect of the invention, the method of disease monitoring is provided for assessing colorectal disease progress.

In a further aspect of the invention, the method of disease monitoring is provided for assessing post-operational recurrencies of colorectal cancer (CRC).

In a further aspect of the invention, the method of disease monitoring is provided for monitoring Inflammatory Bowel Disease (IBD) activity.

In a further aspect of the invention, the method of disease monitoring is provided for assessing conservative therapy efficiency in Inflammatory Bowel Disease (IBD) patients.

In an eighth embodiment of the invention, a method of screening for colorectal cancer (CRC) is provided. The method comprising any of the methods described above and further comprising conclusion on the presence or absence of colorectal cancer in an asymptomatic individual.

In a further aspect of the invention, a method of screening for colorectal cancer (CRC) is provided for self-assessment use.

In another aspect, the invention provides a method for preserving medical or biological specimens taken using a swab, enabling them to be stored temporarily or transported at ambient temperatures with a minimal level of degradation.

The invention includes a standard swab system which can be placed in a hermetically sealed tube after sampling. Preferably, the swab comprises a rod with a tip (i.e. a sample collecting element or sample collection material) made from natural fibres (cotton or rayon) at the distal end and a screw cap at the proximal end, enabling the swab to be sealed in a tube. The tube contains a storage or stabilising medium of various types which can exist in a number of formats depending on application. The swab tip is placed in the medium when the swab is introduced into the tube.

Samples taken for subsequent molecular diagnostic analysis such as PCR, genetic fingerprinting, or protein immunoassays need to be protected against degradation of macromolecules. In this embodiment of the invention, a solution of high salt concentration should be used as the storage or stabilising medium. Such a solution has the effect of precipitating protein in the sample, preventing autolysis. It also inhibits microbial action, preventing putrefaction. A specimen in such a solution will largely remain on the swab tip rather than entering the solution. The first step of a subsequent analysis requires re-suspension of the sample in a buffer which can dissolve its molecular components.

The embodiment of this invention in which a concentrated salt solution is used as the storage or stabilising medium can be provided in a number of formats. The solution may be present in the tube as a simple liquid, but for convenience of handling in the field, it would be preferable to include it as a gel, an impregnated sponge or a liquid medium sealed under a plug of gel.

For combined cytological and molecular analysis of samples, precipitating solutions can also be used since whole cells of eukaryotic or prokaryotic origin are also preserved in such a concentrated salt solution. However, at very high salt concentrations, cell morphology can be compromised. For this reason lower concentration salt solutions, fixatives or commercial preparations such as PreservCyt, used for Pap testing are optimal if samples are being preserved specifically for cytological analysis. These solutions are also mostly compatible with the range of formats listed above—liquid medium, gel, impregnated sponge or medium sealed under a gel plug.

Media for supporting microbiological samples can also be used in an additional embodiment of this invention. Whilst gels based on the formula for Stuart media (e.g. from BD Biosciences) are currently routinely used in hospitals to transport swabs, similar media could be used in liquid formats impregnated into a sponge or sealed under a gel plug if a liquid medium was preferable to a gel for certain types of microorganisms.

BRIEF DESCRIPTION OF THE FIGURES

The present invention will now be described, by way of example only, with reference to the accompanying drawings, in which.

Figure 1:
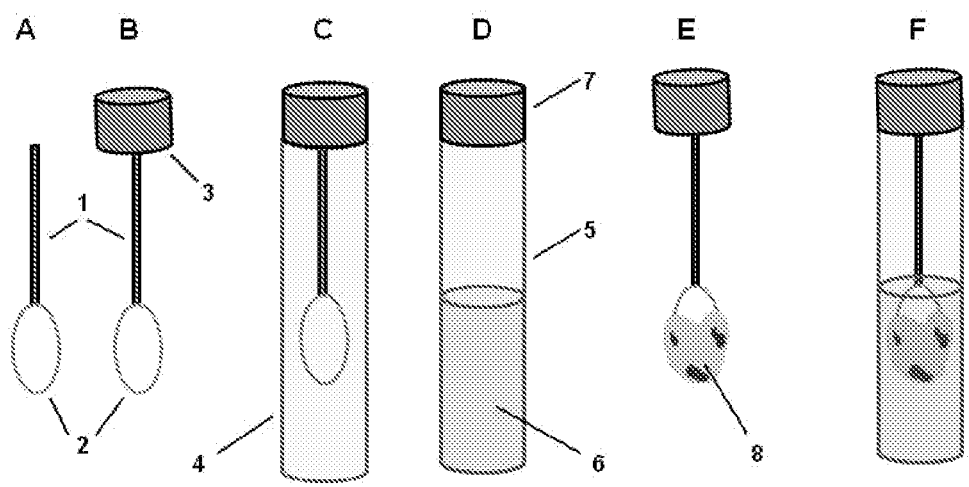
FIG. 1 shows the initial evolution of the simplest version of a device for collecting fragments of large bowel mucocellular layer from the surface of anal/perianal area, which may be a swab (A) consisting of a rod (1) and a piece of absorbing material (sample-collecting element or sample collection material) (2) attached to its distal end. In a more advanced basic version of the sample-collecting device (B) the swab rod (1) is attached to an inner surface of a cap (3) compatible with a laboratory tube.

A laboratory tube (4) with the sample-collecting device inside as it should be supplied for sample collection is shown as (C).

Another laboratory tube (5) containing a buffer or a medium (6) and hermetically closed with a cap (7) is shown as (D). The C and D taken together constitute a basic kit supplied for sample collection.

The basic version of the sample-collecting device with a sample of large bowel mucocellular layer fragments already collected (8) is shown as (E).

The sample collected by the basic version of the device, immersed in buffer or medium and ready to be shipped to a laboratory is shown as (F).

Figure 2:
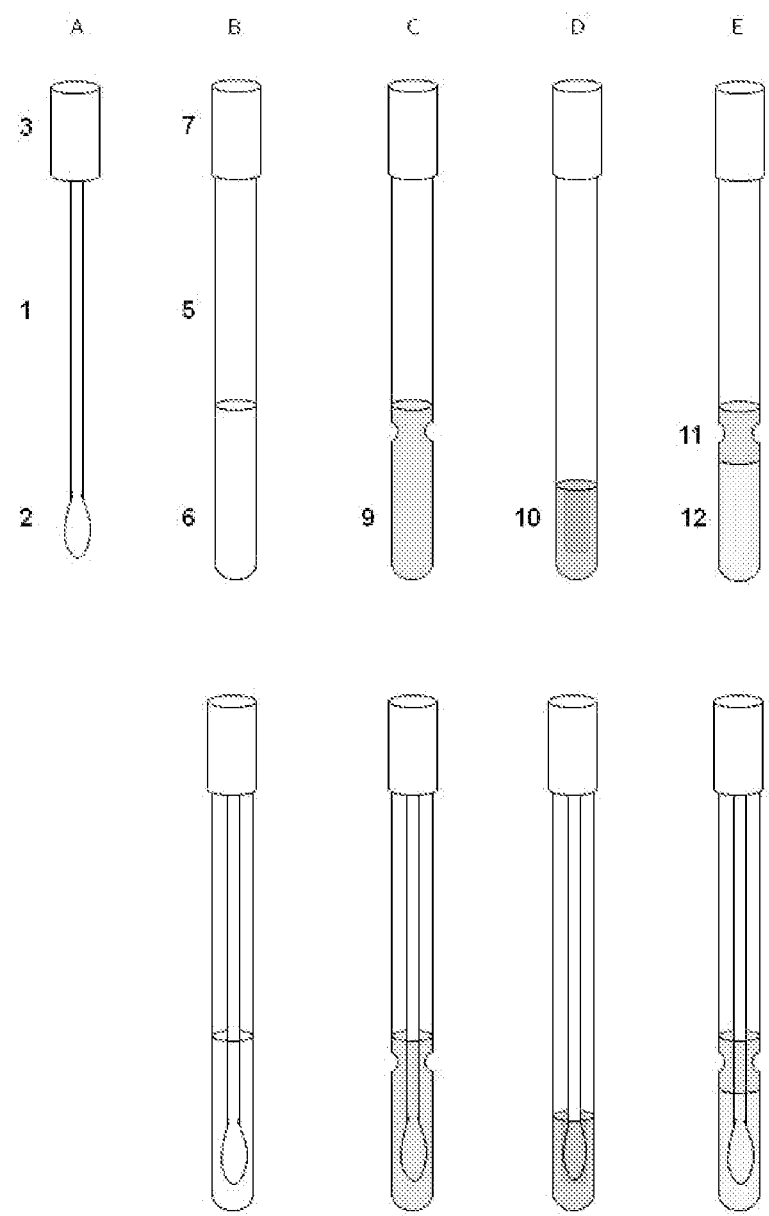

FIG. 2 shows a variant of the basic version of the device (A) and a variety of embodiments of the storage medium in a hermetically sealed tube; a simple liquid medium (B), a gel (C), a medium-impregnated sponge (D) or a medium sealed under a plug of gel (E). In each case the tubes are shown with and without the device in place. Upon sampling, the cap of the medium containing tube (7) is discarded and the device screwed into the tube. The plastic tube (5) can be hour glass shaped to improve the passage of the tip though a gel, or straight in the case of embodiments in which gel is not used. A liquid medium (6) or a gel (9) may be used to preserve and store the specimen. In another embodiment, a medium impregnated sponge is used to preserve the sample (10). The sponge has a cylindrical slot to house the swab tip in contact with the surface of the sponge. In another embodiment, the preserving/storage medium (11) is retained under a plug of gel (12).

Figure 3:
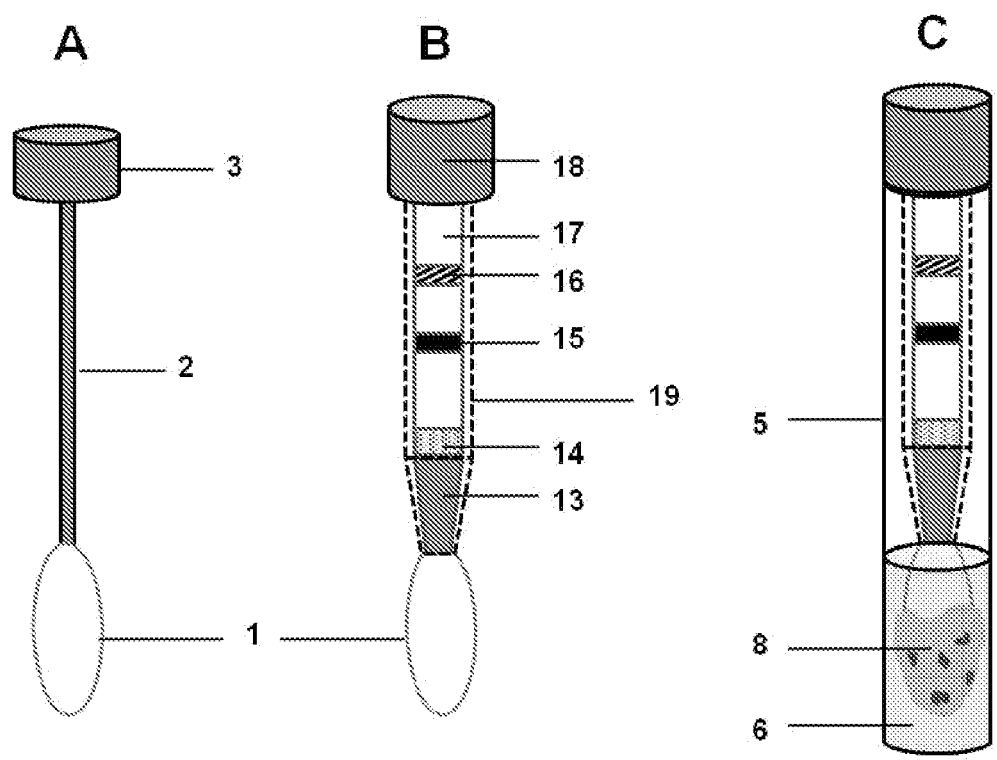

FIG. 3 shows the sample-collecting device in its basic version (A) and an advanced version incorporating a lateral flow test strip forming a lateral flow strip device (B) as well is the lateral flow strip device following sample collection, where sample-collecting element is already immersed in a buffer.

The following elements of the lateral flow strip device (B) are shown:

13—sample pad, the function of which is also in part exerted by the sample-collecting element (2) providing initial sample delivery and filtration due to its absorbing qualities and porosity;

14—conjugate pad. In one embodiment the conjugate pad contains nanoparticles of colloidal gold or latex or carbon etc;

15—test line. In one embodiment the test line contains antibodies specific to a selected target (such as a bowel disease-specific molecular marker) providing a test result, which may be quantifiable (additional test lines with specifically selected detecting agent concentrations can be used for quantitation refinement or multiple biomarker detection);

16—control line providing successful test run confirmation;

17—nitrocellulose membrane providing liquid capillary flow;

18—modified tube cap containing wicking pad (absorbent pad) providing liquid flow through the device;

19—plastic housing protecting the lateral flow strip (it may not be transparent and can contain windows exposing only test (15) and control (16) lines.

Figure 4:
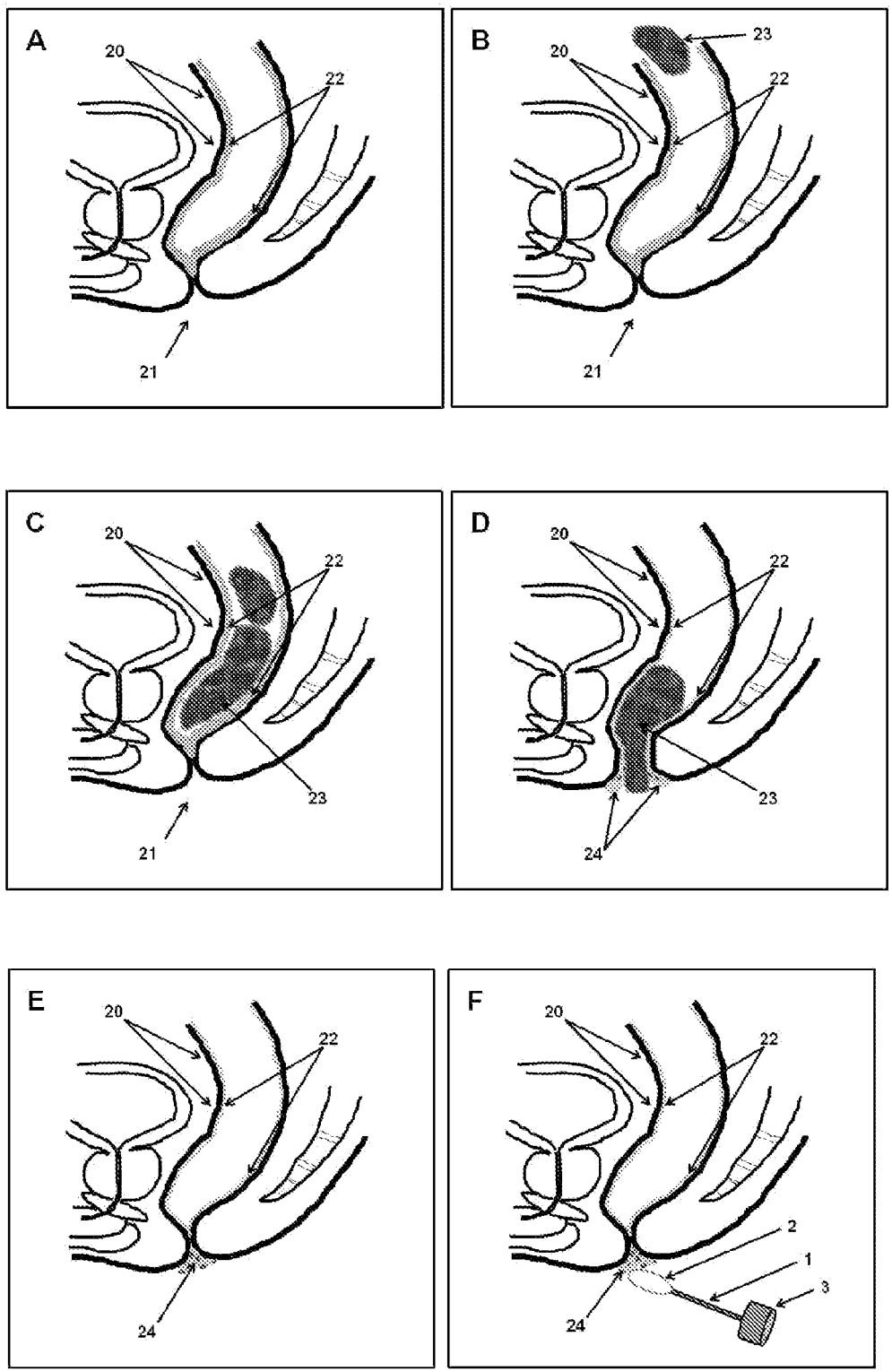

FIG. 4 shows a cross section of the human rectum, anus and adjacent organs

A—The rectum is empty between two normal acts of defaecation. Gradual accumulation of the rectal mucocellular layer is progressing.

20—rectum; 21—anus; 22—rectal mucocellular layer overlaying the rectal mucosa.

B—Stool (23) portions start entering the rectum. At this moment there is no significant contact between stool and the rectal mucocellular layer.

C—The rectum is filled with stool, which comes into a close contact with the rectal mucocellular layer. Muscular contraction of the rectum preceding defaecation enhances this contact.

D—Defaecation. Stool is being evacuated from the rectum by concerted rectal contractions and anal canal opening. A considerable proportion of the rectal mucocellular layer is evacuated together with stool, being predominantly on its surface or on the walls of the anal canal (as an additional lubricant). Fragments of the rectal mucocellular layer (24) remain on the surface of the external anal/perianal area often mixed with stool fragments.

E—Immediately post-defaecation. The rectal mucocellular layer is considerably depleted immediately following defaecation. Its excreted fragments remain on the surface of the external anal/perianal area (and are removed by cleaning unless sample collection is planned).

F—Post-defaecation collection of the excreted fragments of the rectal mucocellular layer using the basic version of the sample-collecting device described in this invention.

Figure 5:

FIG. 5 shows a microphotograph of a single exfoliated colonocyte obtained by self-sampling of large bowel mucocellular layer fragments from anal/perianal area of a healthy volunteer immediately following defaecation. Typical elongated shape of the cell is evident. (Haematoxylin & eosin ×400). Low faecal contamination. Mucus present.

Figure 6:
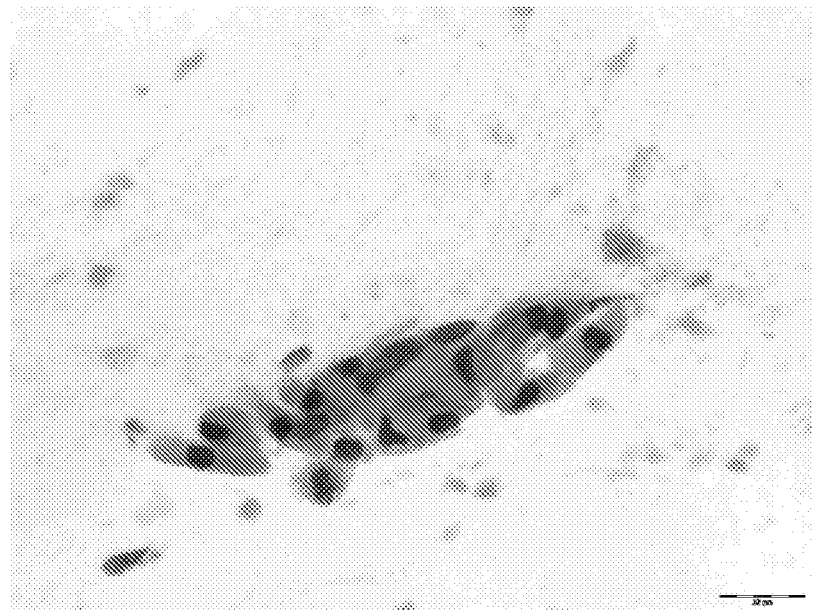

FIG. 6 shows a microphotograph of a group of exfoliated colonocytes obtained by self-sampling of large bowel mucocellular layer fragments from anal/perianal area of a healthy volunteer immediately following defaecation. All cells have typical elongated shape; they are very well preserved. (Haematoxylin & eosin ×400). Low faecal contamination.

Figure 7:
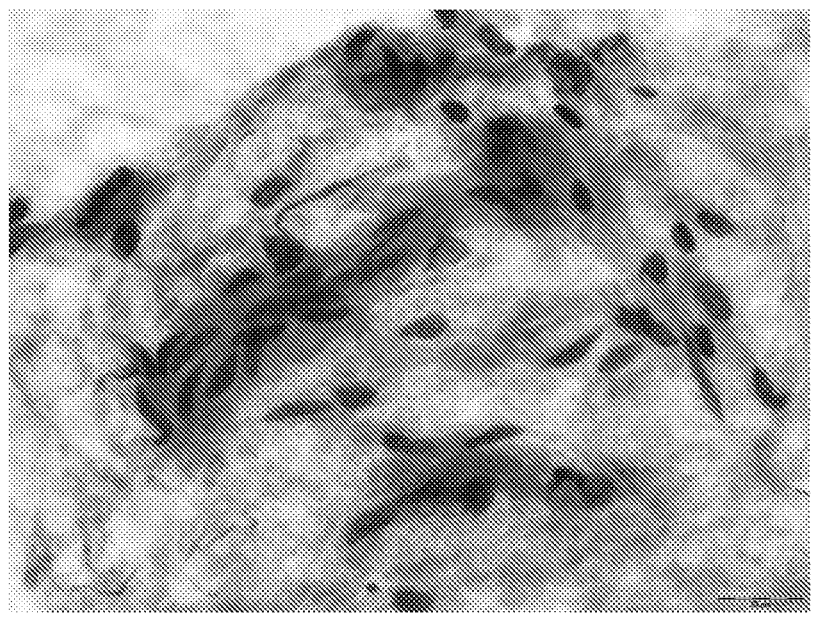

FIG. 7 shows a microphotograph of a large group of exfoliated colonocytes embedded in mucus obtained by self-sampling of large bowel mucocellular layer fragments from anal/perianal area of a healthy volunteer immediately following defaecation. All cells have typical elongated shape. Mucus layer (remnants of the mucocellular layer) slightly obscures some of the cells. (Haematoxylin & eosin ×400). Low faecal contamination.

Figure 8:
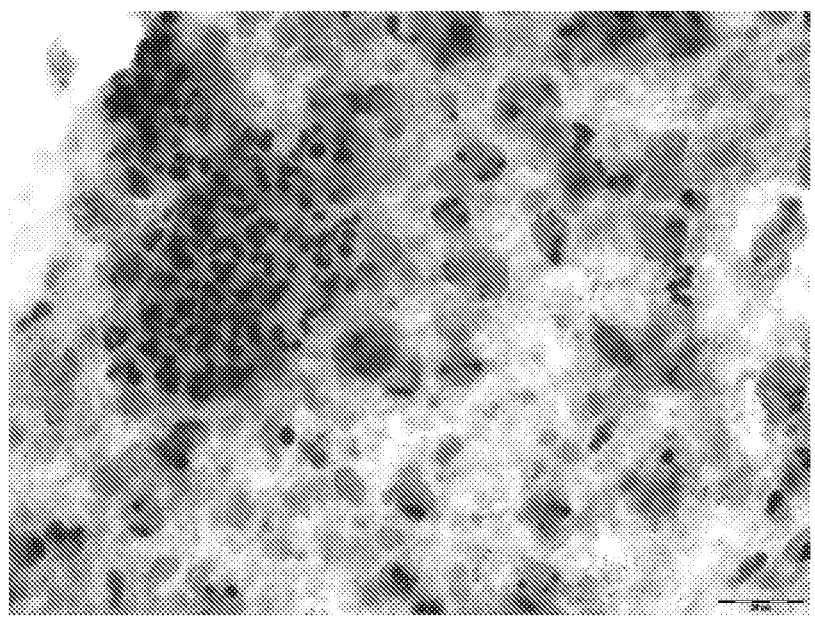

FIG. 8 shows a microphotograph demonstrating abundant presence of neutrophilic leucocytes in mucus obtained by parent-performed sampling of large bowel mucocellular layer fragments from anal/perianal area of an infant affected by an inflammatory bowel condition immediately following defaecation. All neotrophils have typical segmented nuclei. (Haematoxylin & eosin ×400). Low faecal contamination.

DETAILED DESCRIPTION OF THE INVENTION

As previously discussed, there exists a need to develop a non-invasive, simple and inexpensive technique for sampling the mucocellular layer, particularly, the mucocellular layer of the bowel and rectum. We have now identified that a considerable portion of the rectal mucocellular layer is evacuated together with stool, and more importantly, fragments of the mucocellular layer remain on the surface of the external anal/perianal area following defaecation. Usually, these fragments would be removed in the course of cleaning following defaecation. However, it has been identified that these fragments can be successfully collected and subsequently analysed using the material-collecting device described herein.

Basic and Advanced Versions of the Device for Non-Invasive Collection of Large Bowel Mucocellular Layer Fragments Different versions of the material-collecting device disclosed above are presented in FIGS. 1, 2 and 3.

The first embodiment of the invention presents a basic version of the material-collecting device that can be described as a swab consisting of a thin plastic (e.g. polypropylene) rod (1) and a sample material collecting element or tip (2), which should be made of a porous material such as cellulose, cotton wool, nylon, synthetic sponge, flocked nylon etc. The combined length of the rod and material-collecting element (see FIG. 1A) should be about 100 mm, which will make it perfectly compatible with a polypropylene laboratory tube, e.g. a Falcon™ (BD Biosciences) tube.

The material of the sample-collecting element of the device can be selected according to specific purposes of sample collection (e.g. targeting intact cell collection and cytological or in situ analyses, protein and RNA preservation or DNA-related applications). The shape of the sample-collecting element can be oval or round (preferably preventing it from being inserted in the anal canal during sample collection). The width of the sample-collecting element should be within 10 mm, which will allow its compatibility with a laboratory tube.

In the basic version of the sample-collecting device the plastic rod (1) is securely attached to the inner surface of a laboratory tube cap (3) as shown in FIGS. 1B & 2A. The basic version of the device should be stored before use in a hermetically sealed tube as shown in FIG. 10.

The second embodiment of the invention includes incorporation of a lateral flow test strip instead of the rod as shown in FIG. 3B. This modification allows combining functions of sample collection and sample analysis in one device designated here as lateral flow device.

Lateral flow assays constitute a modern family of tests based upon passive liquid transport via capillary forces (Haeberle et al., 2007). These tests presented in the format of microfluidic platforms emerge as a convenient option for various situations requiring point of care testing or self-testing. They are normally manufactured at low cost as disposable assay devices and can be easily adapted to a range of techniques primarily based on immunoassays, but now including hybridization-based DNA-measuring technologies (Mao et al., 2009).

FIG. 3B shows the proposed advanced version of the sample-collection device incorporating a lateral flow strip of a generally used pattern. Whereas analytical components of the assay such as compositions of the conjugate pad (14), test line or lines (15) and control line (16) should be defined according to specific testing targets (e.g. human DNA quantification or specific protein detection), original elements of the design comprise combining sample pad (13) of the lateral flow strip with the sample-collecting element of the device (2) and introduction of a modified tube cap incorporating wicking (absorbent) pad (18). The former feature can provide additional protection from contamination of collected samples with faeces, which can be considerable in some cases.

The lateral flow device described above will be disposable.

Basic and Advanced Versions of the Kit for Non-Invasive Collection of Large Bowel Mucocellular Layer Fragments The third embodiment of the invention introduces the concept of a kit for either sample collection or sample collection and analysis. The basic version of the kit is shown in FIGS. 1C & 1D, where the sample-collecting device is supplemented with a tube containing a buffer or a medium. The buffer should be, again, selected according to testing targets since different buffers or media will be required for cell preservation, protein or nucleic acid analysis. The basic version of the kit is designed for initial sample treatment (fixation, preservation/precipitation or lysis) for its secure storage and transportation to a laboratory for analysis. A range of examples of preserving buffers or media is shown in FIG. 2.

Likewise, buffers should be "tailor-made" for any specific lateral flow tests, which can be performed immediately as shown in FIG. 3C. This would enable sample self-testing if reliable visual reading of the result is made possible. Alternatively the device can be sent to a laboratory, where the result is assessed and interpreted as a point of care test. One possible further option may be collecting material using the basic version of the kit and applying the lateral flow device in a laboratory as a point of care test.

DNA analysis may constitute a very important application for samples of large bowel mucocellular layer, therefore specific sequence amplification option may be a desirable addition to the kit, especially in the form of the loop-mediated isothermal amplification (LAMP).

Method of Non-Invasive Collection of Large Bowel Mucocellular Layer Fragments

The fourth embodiment of the invention defines a method of sampling fragments of large bowel mucocellular layer from the surface of the anal/perianal area immediately following the natural act of defaecation. Physiological mechanisms behind this approach are presented in FIG. 4.

It is evident that the existence and role of the mucocellular layer in the human large bowel is presently largely overlooked with only a few relevant publications (Loktionov, 2007; Loktionov et al., 2009; Loktionov et al., 2010).

FIGS. 4A & 4B shows that when the rectum is empty between two acts of defaecation the rectal mucocellular layer is not affected by the presence of faeces, which was demonstrated by its intrarectal collection (Loktionov et al., 2009; Loktionov et al., 2010). Once the rectum is filled with stool (see FIG. 4C), the mucocellular layer comes into a close contact with stool, which is further enhanced by muscular contraction of the rectum preceding defaecation. This results in partial attachment of the mucocellular layer to excreted stool. This part of the mucocellular layer is then evacuated together with stool (FIG. 4D). The phenomenon is reflected by the easily detectable presence of mucocellular layer elements on the surface of excreted stool (Loktionov et al., 1998; Bandaletova et al, 2002). At the same time it has been found that the position of the mucocellular layer between the intestinal wall and excreted faeces leaves a considerable part of the cell-containing mucus on the surface of the anal canal and eventually on the surface of the anal and perianal area (see FIGS. 4D & 4E). Although faecal contamination of various degrees is also present in this area following defaecation, the presence of colon-derived cellular material is significant (see FIGS. 5-8 below). These conditions create an excellent opportunity for non-invasively collecting mucocellular layer fragments from the anal/perianal area as shown in FIG. 4F. Collection of mucocellular layer fragments from this site has never been attempted before.

It should also be noted that the rectal mucocellular layer should be depleted following defaecation. This view is supported by a previous observation of much poorer results of a test based on intrarectal exfoliated cell collection if mucocellular layer was sampled following bowel preparation (Loktionov et al., 2009). For this reason the necessity of the distinct physiological act of defaecation as a prerequisite for sample collection according to the method disclosed in this invention constitutes an important natural standardizing factor. Furthermore, the necessity of collecting samples immediately after defaecation makes sample self-collection the preferable way of using the device. It should also be stressed that absolute non-invasiveness of the sample collection method makes repeated sample collection extremely easy (it can be repeated following the next defaecation without any harm).

Once a sample of the rectal mucocellular layer is collected, it is placed in a tube with a buffer or medium as demonstrated in FIGS. 1F, 2 & 3C for the basic and advanced versions of the device. Then the sample can be either shipped to a laboratory for analytical assessment or immediately analysed using a lateral flow assay. The latter option exists only for the advanced version of the device.

Although the device of this invention is primarily designed for mucocellular layer fragment collection from the surface of the anal area, it can also be applied for collecting body liquid/biological samples from other body orifices such as urethra, vagina, nostrils, external ear and oral cavity. Moreover it is evident that urethral sample collection can be done immediately following the physiological act of urination.

Methods of Sample Analysis

The fifth embodiment of the invention introduces a wide range of sample analysis methods, which can be applied to collected samples. The main methods considered in view of potential clinical applications of the approach comprise direct DNA quantitation, DNA isolation followed by quantitation and molecular analysis, RNA isolation followed by molecular analysis or quantitative gene expression analysis, protein quantification by immunoassays and cytological and immunocytochemical investigation.

All these methods apart from cytological/immunocytochemical investigations can be applied using appropriately prepared versions of lateral flow strip devices. This additionally allows testing for an extremely wide range of diagnostically important biomarkers.

One potential problem is the presence of variable levels of faecal contamination in samples of the rectal mucocellular layer. Faecal contamination is known to be an interfering factor in earlier proposed tests for CRC based upon quantitation of DNA in exfoliated colonic cell samples collected intrarectally (Loktionov et al., 2009; Loktionov et al., 2010). This problem can be solved either by using selective quantitation of human-specific DNA in the presence of contaminating non-human DNA molecules in the lateral flow strip assay (Mao et al., 2009) or through application of recently introduced PCR-based kits for selective human DNA quantitation such as Quantifier Human DNA Quantification kit from Applied Biosystems or AluQuant Human DNA Quantitation System from Promega.

Sample analysis methods may be of different degrees of complexity, but the use of the advanced version of the device equipped with lateral flow strip should allow rapid sample testing in the format of point of care tests. Development of a disposable self-testing kit (e.g. based upon direct DNA quantification lateral flow assay) suitable for CRC self-detection can also be considered in this context.

Disease Detection Applications

The sixth embodiment of the invention is related to disease detection in symptomatic patients. The approach to sample collection and analysis related to this invention predominantly focuses on colorectal disease, in particular CRC and IBD. Existing information (see background section) indicates that the use of cellular elements of the large bowel mucocellular level can be much more informative for CRC detection compared to FOBT. DNA-related CRC biomarkers appear to be the most adequate from this point of view. The use of human-specific DNA quantitation can be regarded as the most promising among existing approaches, therefore its application should be regarded as the first priority. Further methods, comprising detection of gene-specific hypermethylation of regulatory region and mutation analysis can also be considered as well as some protein-based assays such as M2-PK detection.

The same approach can be applied to advanced colorectal polyp detection.

The sample collection method constituting the essence of this invention also allows diagnosis of anal cancer, which can be detected either by using methods quoted for CRC detection or by cytological analysis of collected samples.

Inflammatory bowel disease constitutes another major target of the approach. Although these conditions also result in dramatically increased DNA presence in collected samples, the use of protein markers such as calprotectin, eosinophil-derived neurotoxin, soluble cytokeratin-18 etc. may be more informative for both detection and differential diagnosis of different conditions within this group.

Disease Monitoring Applications

The seventh embodiment of the invention targets disease monitoring, in particular monitoring of chronic colorectal conditions. Surveillance of post-operational CRC cases is a major task, and the approach presented in this invention can be extremely useful in timely detection of local CRC recurrencies. The methodological strategy in this setting should be the same as described above for CRC detection.

Monitoring of chronic IBD cases might constitute even wider area of application. Repeated sampling followed by protein analysis (e.g. simple calprotectin test) can considerably help in detecting early relapse in these patients, which can result in immediate therapeutic treatment. Likewise, repeated testing can help in assessing conservative therapy efficiency in these patients. The use of semi-quantitative lateral flow assay allowing inflammation activity measurement is essential for this purpose.

CRC Screening

The eighth embodiment of the invention focuses on CRC screening. The approach has necessary features of an ideal cancer screening test, being absolutely non-invasive, safe, simple, inexpensive, easily repeatable, and self-applicable. Using the advanced version of the sample collection device equipped with the lateral flow strip, it can be applied in a point of care test format, which would be perfectly suitable for population screening programmes. The ultimate CRC screening application may be achieved with the introduction of the self-assessment version of the test.

The initial application of the basic version of the sample-collecting device is illustrated by EXAMPLE 1.

Example 1

A group of four healthy volunteers performed repeated collections of the large bowel mucocellular layer fragments from the surface of the anal/perianal area immediately following defaecation. The basic version of the sample-collecting device has been used. Collected samples were immediately used for preparing smears on microscope slides. The smears were fixed with Surgipath cytological fixative (Leica Microsystems) and stained with haematoxylin and eosin. Microphotographs have been made using Olympus DP-72 camera.

FIGS. 5, 6 & 7 show the presence of clearly identifiable colonocytes, which could be easily found in each prepared smear. Given that all the volunteers did not have colorectal complaints, the results of the new sampling technique are perfectly comparable to those previously described for healthy volunteers when exfoliated material was collected intrarectally using a device introduced through a proctoscope and equipped with an inflatable membrane (Loktionov et al., 2009; Loktionov et al., 2010).

In addition, material was collected from the surface of the anal/perianal area of an infant suffering from an acute inflammatory bowel condition. Material collection has been performed by the mother of the baby. FIG. 8 demonstrates abundant presence in the sample of neutrophilic leucocytes, which are typical for active inflammation process.

Method and Device for Preserving Medical or Biological Specimens

Swabs are widely used in the fields of clinical and diagnostic analysis, biological research and forensics for the purpose of sampling a biological material for later analysis in a suitably equipped laboratory. Transit of high quality, undegraded samples to a laboratory is critical to the quality of results in a multitude of different forms of testing.

Currently used swabs usually consist of a natural fibre tip (often cotton or rayon) on the end of a cylindrical plastic or wooden rod. In some incarnations, at the upper end, the rod is connected to a tube cap which enables the swab to be enclosed in a tube after sampling. An ideal device must provide efficient gathering and recovery of bacteria, viruses, spores, eukaryotic cells, proteins, nucleic acids and a variety of other biological entities. US Pat. App. Nos. 2004/0267181 and U.S. Pat. No. 8,114,027 suggest designs for swab based sampling systems. Using a fibre with hydrophilic properties such as flocked nylon described in U.S. Pat. No. 8,114,027 by Triva can be very efficient for collecting eukaryotic cells.

Perhaps the most common use for such devices is gathering microbiological specimens. U.S. Pat. Nos. 4,529,702 and 5,096,062 describe a device and media for this purpose. For microbiological sampling, the swab is placed into a tube for transportation which contains a medium or gel formulated to support the sample with a view to subsequent culturing. Such media contain buffering salts, but lack nutrient sources of carbon and nitrogen, with the aim of keeping all microorganisms in the sample alive, without encouraging proliferation. Stuart medium is a commonly used agar based medium for microbial transport.

The approach used by microbiologists has a limited usefulness for diagnostic samples however, since it will not protect less robust cells and easily lysed molecules from sustaining damage between sampling and analysis. In this case, damage is caused by autolysis (molecular breakdown caused by digestion by enzymes present in the specimen) or putrefaction (attack by microbiological agents found in the sample or acquired from the environment). Typically, for diagnostic samples, degradation is avoided by flash freezing (freezing quickly to avoid the development of ice crystals in a sample) or the use of enzyme inhibitors. However, in many instances a method for subjecting a specimen to cryogenic temperatures is not available or convenient, and inhibitors tend to have a limited effectiveness.

Some prior art exists relating to the preservation of cells and diagnostic molecules in biological samples. U.S. Pat. No. 5,256,571 for example suggests a water-miscible alcohol solution including a buffer and anti-clumping agent for the preservation of cells. PreservCyt™ (Cytyc Corp.) is a commercially available methanol and water based cell preservation system, which is widely used in Pap smear testing. While alcohol-water based media may be able to fix cells for later cytological analysis, they are not effective for preserving RNA and protein at ambient temperatures.

Complex buffering systems are also used to preserve the physiological activity of tissues separated from their normal blood supply. These typically consist of isotonic solutions containing additional salts, sugars, local anaesthetic and other agents, which are designed to support a tissue or organ at below physiological temperatures at which their metabolic rate is significantly lowered. U.S. Pat. Nos. 5,432,053, 4,879,283 and 5,565,317 are examples of patents in this area. U.S. Pat. No. 7,220,538 describes a tissue and organ maintenance system based on buffering solutions including liposomes and various nanoparticles which can provide support and nutrition over substantial time periods without the need for chilling. Whilst claims are made that these solutions preserve intact cell structures and nucleotides, it is unlikely that any of these proposed solutions could effectively prevent autolysis in samples which did not consist of discrete organs and tissues or were partially degraded or contaminated for example.

U.S. Pat. No. 6,204,375 proposes the use of solutions containing high concentrations of ammonium sulphate to preserve RNA in cell and tissue samples.

The present invention also relates to methods and devices for preserving medical or biological specimens taken with a swab. The method enables the lifespan of samples kept at ambient temperature to be substantially extended. The most likely use of the invention is as a sample transport method and temporary storage, in which specimens are preserved between sampling and arrival at an appropriately equipped laboratory.

The present invention requires a sample to be gathered on a swab tip, the tip then introduced into a tube where it comes into contact with a storage or stabilising medium. The medium used could be in the form of a simple liquid, but preferably could be in the form of a gel, an impregnated sponge or a liquid medium with a plug of gel above it to retain the medium at the bottom of the tube. The primary advantage of a gel, a sponge or a medium with a gel plug is the convenience of avoiding spilling the medium when used in the field (for example, a specimen taken during an operation or at a crime scene, or medical self sampling by untrained individuals at home). In addition, using these approaches, samples are retained cleanly at the bottom of the tube and in the case of a gel or a sponge, the specimen remains largely on the tip rather than diffusing into the storage or stabilising medium.

In one embodiment of this invention in which an impregnated sponge is used to support or preserve the sample, PVA would be the preferred material from which to make the sponge, since it is highly absorbent of water based solutions. The sponge should be designed with a slot in which the swab tip rests when the swab is placed in the tube, meaning that the tip is surrounded by and in contact with the medium within the sponge.

In one embodiment in which a gel plug is used above a medium, when the used swab is placed in the tube, the tip will penetrate the gel, exposing the sample to the medium below. An additional advantage of this approach is that even once the plug has been penetrated by a tip, there may be little or no leakage of the medium through the gel. This means that the tip bearing the sample remains in contact with the medium, even if a small amount of medium is in the tube and regardless of the tube's orientation.

While the methods used to prepare the media and gels described in this patent should be known to the skilled person, the method for preparing the gel plug may be less clear. The gel can be made from any gelling agent, including (but not restricted to) agar, gelatine, polyacrylamide, pectin, polyethylene glycol, guar gum or locust bean gum. The gel concentration should be sufficient to form a solid plug, but not high enough to prevent easy penetration by a swab tip. In the case of agar, a 0.25-3% gel may be used, but around 0.5-1% appears to be optimal, depending on the size of the plug. The gel solution is heated and added to the medium to be used, at the bottom of the collection tube. A liquid gel is non miscible with most other liquid solutions. With water based salt solutions, the density of a gel made up in water will generally be lower than that of the solution, and as it cools the gel will form a solid layer above the medium. With lower density liquids (alcohols for instance) or a higher density gel formula, the gel plug will form below the medium. This problem can potentially be overcome by adjusting the gel concentration (and density), using a lower density gel formula or allowing the gel to cool with the tubes placed upside down.

The optimal storage or stabilising medium to use with this invention depends on the sample type and the analysis which will be performed downstream. In the case of molecular analysis, or a single specimen for which combined cytological and molecular analysis will be performed, the optimal medium may be a concentrated salt solution which has the effect of wholly or partly precipitating the sample, thus inhibiting or preventing lysis. The preferred salt for bringing about sample precipitation is ammonium sulphate, but other salts may also be used. Ions are ranked in a series known as the Hofmeister series, which orders their ability to precipitate (salt out) proteins at one end of the scale and dissolve and denature (salt in) at the other. Both ammonium and sulphate ions have a high level of ability to interfere with the interactions between water and protein molecules, making proteins in ammonium sulphate solutions less soluble. Ammonium sulphate is itself highly water soluble, making it possible to form a very concentrated solution. Other highly soluble salts with the ability to salt out proteins may also be used, including but not restricted to sodium citrate, ammonium bisulphate, ammonium acetate or sodium chloride. Precipitated lytic enzymes, such as nucleases and proteases are rendered enzymatically inactive and are thus unable to degrade other components of a sample. The authors suggest that media (liquid or gel) containing high concentrations of salts, such as 25% or higher v/v ammonium sulphate will inhibit the development of microorganisms, further contributing to the preservation of samples. This feature would be of particular benefit when using contaminated samples, such as infected or necrotic material or fecal samples.

Once the period of transport or storage is over the swab tip bearing the sample can be removed from the high salt storage medium and transferred into a buffer which redissolves proteins. This may for instance be a physiological buffer, for cytological analysis, or a detergent containing lysis buffer, for molecular analysis. If the method is being used to preserve nucleic acids, it is likely that the use of such a high salt solution would precipitate the nucleic acid along with sample proteins, so a redissolving buffer would redissolve both protein and target nucleic acid.

The solubility of proteins at high ionic strength differs markedly. In general, a more concentrated salt solution precipitates more proteins and protects samples more effectively. Thus the most effective method of preventing lysis of informative molecules may be the embodiment of this invention in which saturated ammonium sulphate is used as a liquid or impregnated into a sponge surrounding the swab tip when placed in a tube. Indeed, studies show that in more stringent conditions, a higher (preferably saturation) ammonium sulphate concentration is required to preserve molecular integrity—lower salt concentrations delay sample degradation rather than prevent it. However, very high concentrations of ammonium sulphate can cause irreversible damage to cellular structure. So if cytological analysis is also to be performed, lower salt concentrations appear to be preferable. Thus, the exact format in which this system should be used is application-dependent. Buffering salts beyond ammonium sulphate may also be added to the preservation solution if required to stabilise specific molecules of interest in a sample.

An additional advantage of buffers containing high salt concentrations which prevent dissolution of samples is that a soluble specimen on a swab immersed in such a buffer will not dissolve and disperse into the medium. Instead it remains largely intact on the swab during transport and can later be redissolved by transferring the swab tip into another buffer.

In one embodiment of this invention in which the salt solution is in the form of a gel, the salt concentration is limited by the necessity to dissolve the gelling agent. If ammonium sulphate is used as the precipitating salt, the essential components of the gel are up to 25% ammonium sulphate v/v (approx 15-17 g per 100 ml) and up to 0.25% agarose w/v (acrylamide, gelatine or pectin could also be used as a gelling agent). Other stabilising salts could be added, but in this case a reduction in the ammonium sulphate concentration may be required or the presence of extra solute will reduce the solubility of the agarose, making the gel more liquid. This formula contains the minimal amount of agar required to set the solution as a gel, which means that the gel more effectively wets the swab tip.

In one embodiment of this invention in which a gel plug is used above a sample medium is compatible with transporting samples for diverse purposes and in differing media. The media may include but are not restricted to; high salt precipitation media for molecular preservation (as discussed elsewhere in this patent), histological fixatives such as alcohol or aldehyde based solutions, cytological transport media for preserving the integrity of eukaryotic cells (such as the commercially available PreservCyt™ (Cytyc Corp.) or Cytoport (Gentaur) or liquid microorganism transport media.

Using agar seals is a known method in microbiology, which is often applied to prevent oxygenation of anaerobic media or, to prevent agitation of a growing medium or to trap gasses produced by a culture. In this invention, the method is suggested as a convenient method of sampling and transporting microorganisms in a liquid phase. The presence of the gel seal may be useful to prevent the media from being exposed to the air, and a large and soft gel may help to reduce exposure of a sample to the air once it is in the medium.

In the case of microorganism transport media or cytological transport media under a gel plug, it is likely that the media will dissolve the sample, removing it from the swab tip over time. That being so, the sample must be recovered by pipetting the media from the tube. This should be easily accomplished by penetrating the gel with a pipette tip. The invention is potentially usable for preserving the integrity of any medical or biological sample which can be gathered on a swab tip. This includes, but is not restricted to blood, saliva, faeces, urine, skin or any sort of mucus and exudate (for example from the gastrointestinal, respiratory and genital tract) originating from any type of organism. Variations of the method described herein can preserve the structure and molecular integrity of prokaryotic and eukaryotic cells and complex molecules, both intracellular and extracellular. This includes mammalian cells, proteins and nucleic acids.

Further aspects of the invention are defined in the following clauses:

1. A device for collecting fragments of large bowel mucocellular layer from the surface of anal/perianal area of a subject immediately following the natural act of defaecation.
2. A device according to clause 1 in a form of a swab consisting of a rod and a piece of absorbing material as a sample-collecting element attached to its distal end.
3. A device according to clause 1 wherein the proximal end of the said swab rod of the device is attached to the inner surface of a screw cap compatible with a laboratory tube.
4. A device according to clause 1 wherein the rod of the swab is replaced with a lateral flow test strip forming a lateral flow strip device.
5. A lateral flow strip device according to clause 4 wherein the distal end of the lateral flow strip is attached to a screw cap.
6. A lateral flow strip device according to clause 4 wherein the said screw cap contains a wicking pad for the lateral flow strip.
7. A device according to clauses 1 or 4 wherein the device is placed in an empty laboratory tube compatible with the screw cap of the device.
8. A device according to clauses 1 or 4 and 7 wherein the device placed in the laboratory tube constitutes a device-containing element of a kit.
9. A kit comprising the device-containing element according to clause 8 and a similar laboratory tube containing a buffer or a medium.
10. A kit according to clause 9 wherein the buffer is a cell-preserving or fixing medium providing cell structure preservation for further cytological or immunocytochemical analysis.
11. A kit according to clause 9 wherein the buffer is a medium providing protein and RNA stabilisation for further protein and/or RNA analysis.
12. A kit according to clause 9 wherein the buffer is a lysis buffer providing cell lysis and biomolecule release for further analysis.
13. A kit according to clause 9 wherein the lateral flow strip device of the kit contains an immunoassay for quantitative identification of proteins.
14. A kit according to clause 9 wherein the lateral flow strip device of the kit contains components for DNA hybridization reactions for qualitative and quantitative identification of DNA.
15. A kit according to clause 9 wherein the lateral flow strip device of the kit contains components for selective quantitative identification of human DNA.
16. A kit according to clause 9 wherein the kit contains reagents for performing polymerase chain reaction (PCR) comprising oligonucleotide primers.
17. A kit according to clause 9 wherein the kit contains reagents for performing a loop-mediated isothermal amplification (LAMP).
18. A kit according to clause 9 suitable for collecting biological samples from the natural body orifices including urethra, vagina, nostrils, external ear and oral cavity, and in particular anus.
19. A kit according to clauses 9 and 18 suitable to use on animals, and in particular humans.
20. A kit according to clauses 9 and 18 suitable for sampling fragments of the large bowel mucocellular layer containing exfoliated cells originating from colon from the surface of the anal and perianal area immediately following the natural act of defaecation.
21. A method of sampling fragments of large bowel mucocellular layer from the surface of the anal and perianal area of a subject immediately following the natural act of defaecation.
22. A method of sampling according to clause 21 wherein a sample is collected by bringing a collecting device according to clauses 1 and 4 into contact with the fragments of the large bowel mucocellular layer on the surface of the anal and perianal area of a subject immediately following the natural act of defaecation.
23. A method of sampling according to clauses 21 and 22 wherein a sample-collecting device with a collected sample is inserted in a tube containing a medium or a buffer.
24. A method of sampling according to clauses 21-23 wherein a sample-collecting element of a sample-collecting device is immersed in a medium or a buffer.
25. A method of sampling according to clauses 21-24 wherein a tube containing a sample-collecting device a medium or a buffer and a collected sample is hermetically sealed following sample collection.
26. A method of sampling according to clauses 21-25 wherein a sample is self-collected.
27. A method of sample analysis with the purpose of detecting and quantifying cells and biomolecules present in a sample obtained according to clauses 21-26.
28. A method of sample analysis according to clause 27 wherein analytical procedures are selected from direct DNA quantitation, DNA isolation, quantitation and molecular analysis, RNA isolation and molecular analysis, protein quantification by immunoassays or cytological investigation.
29. A method of sample analysis according to clauses 27 and 28 wherein sample analysis can be performed using the lateral flow strip device according to clauses 4 and 9.
30. A method of sample analysis according to clause 29 wherein the method of sample analysis on the lateral flow strip device is an immunoassay for quantitative identification of a specific protein.
31. A method of sample analysis according to clause 29 wherein the method of sample analysis on the lateral flow strip device is a DNA hybridization-based assay for quantitation of a specific DNA sequence.
32. A method of sample analysis according to clause 29 wherein the method of sample analysis on the lateral flow strip device is the selective quantitation of human-specific DNA in the presence of contaminating non-human DNA molecules.

33. A method of sample analysis according to clauses 27 and 28 wherein the method of sample analysis involves DNA amplification using PCR.
34. A method of sample analysis according to clause 33 wherein the PCR is a loop-mediated isothermal amplification (LAMP).
35. A method of sample analysis according to clauses 29-32 wherein the method of sample analysis can be performed as a "point of care" test.
36. A method of sample analysis according to clauses 29-32 wherein the method of sample analysis can be performed as a self-testing assay.
37. A method of disease detection in symptomatic patients providing a conclusion on the presence or absence of a disease.
38. A method of disease detection according to clause 37 wherein the method of disease detection is provided for detecting colorectal disease.
39. A method of disease detection according to clause 37 wherein the method of disease detection is provided for detecting colorectal cancer.
40. A method of disease detection according to clause 37 wherein the method of disease detection is provided for detecting anal cancer.
41. A method of disease detection according to clause 37 wherein the method of disease detection is provided for detecting Inflammatory Bowel Disease.
42. A method of disease detection according to clause 37 wherein the method of disease detection is provided for detecting advanced colorectal polyps.
43. A method of disease monitoring providing a conclusion on the progress of a disease.
44. A method of disease monitoring according to clause 43 wherein the method of disease monitoring is provided for assessing colorectal disease progress.
45. A method of disease monitoring according to clause 43 wherein the method of disease monitoring is provided for assessing post-operational local recurrencies of colorectal cancer.
46. A method of disease monitoring according to clause 43 wherein the method of disease monitoring is provided for monitoring Inflammatory Bowel Disease activity.
47. A method of disease monitoring according to clause 43 wherein the method of disease monitoring is provided for assessing conservative therapy efficiency in Inflammatory Bowel Disease patients.
48. A method of colorectal cancer population screening providing conclusion on the presence or absence of colorectal cancer in an asymptomatic individual.
49. A method of colorectal cancer population screening according to clause 48 wherein colorectal cancer detected by self-assessment.
50. A method for preserving biological specimens taken with a swab.
51. The method of clause 50 comprising a preserving medium into which the swab is placed after sampling.
52. The medium of clause 51 being in the format of a gel.
53. The medium of clause 51 being impregnated into a sponge which comes into contact with the swab tip bearing the specimen.
54. The medium of clause 51 being in the format of a liquid sealed with a gel plug.
55. The medium of clause 51 consisting of a high salt solution for the purpose of precipitating protein, thereby preventing enzymatic degradation of the specimen.
56. The salt solution of clause 55 being ammonium sulphate.
57. The medium of clause 51 being a fixative or cytoprotecting medium for subsequent cytological analysis
58. The medium of clause 51 being a less concentrated salt solution than that specified in clause 6 designed to provide some protection for both molecular and cellular components of the sample.
59. The gel of clauses 52 and 54 being agar, gelatine, pectin, polyethylene glycol, guar gum, locust bean gum or carboxymethyl cellulose.
60. The swab of clause 50 where in the swab is enclosed in a hermetically sealed tube after sampling.
61. A method of rendering a swab sample preserved according to clause 51 available for subsequent analysis; the method, depending on the preserving medium used, being lysing or otherwise resuspending the material on the swab tip in a suitable formulated buffer, transfer of material onto a slide, or recovery of the preserving medium.

The invention claimed is:

1. A non-invasive method for collecting a sample of intestinal or bowel cells or cell fragments comprising:
   taking a swab of mucocellular layer material that originates from said bowel or intestine and is excreted during defaecation, from the exterior surface of the anal area in the vicinity of the exterior opening of the anal canal, wherein said swab is taken following defaecation; and
   (a) collecting the sample of intestinal or bowel cells or cell fragments from the swab of mucocellular layer material, wherein collecting includes transferring the sample of intestinal or bowel cells or cell fragments from the swab of mucocellular layer material into a medium for sample storage or lysis; and analysing said mucocellular layer material from said sample for the presence of one or more bowel disease-specific markers or analyzing cell morphology of the mucocellular layer material; or
   (b) collecting a sample of intestinal or bowel cells or cell fragments from the swab of mucocellular layer material and analyzing cell morphology of the mucocellular layer material.

2. A method as claimed in claim 1 wherein the swab is taken within 5 minutes of defaecation and prior to cleaning the anal area.

3. A method as claimed in claim 1 wherein if (b), then further comprising placing said swab of mucocellular layer material in a storage or lysis medium.

4. A method as in claim 1, wherein if (b), then wherein the method further comprises analysing said sample for the presence of one or more bowel disease-specific markers.

5. A method as claimed in claim 4 wherein said analysing comprises analysing the cell morphology and/or detecting the presence of and/or quantitatively or semi-quantitatively measuring one or more disease-specific molecular markers.

6. A method for screening for or diagnosing bowel disease using the method of claim 1.

7. A method for monitoring bowel disease using the method of claim 1.

8. A method as claimed in claim 1, wherein the bowel disease is selected from the group consisting of colorectal cancer, inflammatory bowel disease, anal cancer and advanced colorectal polyps.

9. A method as claimed in claim 1 wherein said swab comprises a porous sample collection material coupled to a lateral flow assay system.

10. A method as claimed in claim 1 wherein said medium for lysis further comprises oligonucleotide primers specific for bowel disease-specific genetic markers and reagents for performing isothermal PCR.

11. A method as claimed in claim 1 wherein the swab further comprises a gel plug.

12. A method as claimed in claim 9, wherein said swab further comprises a sample holder with a cap, wherein said lateral assay system comprises a lateral assay strip between said cap and said sample collection material and wherein said cap includes a system to promote capillary action.

13. A method of assessing the efficiency of bowel disease treatment using the method described in claim 1.

14. A method as claimed in claim 13, further comprising evaluating the level of activity of bowel inflammation.

15. A method as claimed in claim 3, wherein the storage medium comprises a concentrated salt solution.

16. A method as claimed in claim 3, wherein the storage medium is a liquid or gel.

17. A method as claimed in claim 15, wherein the storage medium is a liquid or gel.

18. A method as claimed in claim 15, wherein said salt solution is ammonium sulphate.

19. A method as claimed in claim 15, wherein said salt solution is non-saturated.

20. A method as claimed in claim 16, wherein the storage medium is a gel, and wherein the gel further comprises a gelling agent.

21. A method as claimed in claim 20, wherein the gel comprises no more than 25% ammonium sulphate v/v and no more than 0.25% agarose w/v.

22. A method as claimed in claim 6, wherein the bowel disease is selected from the group consisting of colorectal cancer, inflammatory bowel disease, anal cancer and advanced colorectal polyps.

23. A method as claimed in claim 7, wherein the bowel disease is selected from the group consisting of colorectal cancer, inflammatory bowel disease, anal cancer and advanced colorectal polyps.

24. A method as claimed in claim 9, wherein said porous sample collection material is flocked nylon.

25. A method as claimed in claim 9, wherein said assay system is an immunoassay or a nucleic acid hybridisation assay.

26. A method as claimed in claim 9, wherein said assay system comprises at least one test line.

* * * * *